(12) United States Patent
To et al.

(10) Patent No.: US 8,993,041 B2
(45) Date of Patent: Mar. 31, 2015

(54) TASTE MASKED ACTIVE PHARMACEUTICAL POWDER COMPOSITIONS AND PROCESSES FOR MAKING THEM

(71) Applicant: New Jersey Institute of Technology, Newark, NJ (US)

(72) Inventors: Daniel To, North Wales, PA (US); Rajesh N. Dave, Princeton, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 41 days.

(21) Appl. No.: 13/651,829

(22) Filed: Oct. 15, 2012

(65) Prior Publication Data
US 2014/0106058 A1    Apr. 17, 2014

(51) Int. Cl.
*A61K 9/50* (2006.01)
*B05D 1/24* (2006.01)
*B05D 7/00* (2006.01)

(52) U.S. Cl.
CPC .............. *A61K 9/501* (2013.01); *A61K 9/5026* (2013.01); *A61K 9/5042* (2013.01); *A61K 9/5089* (2013.01)
USPC ......... 427/2.15; 427/2.14; 427/212; 427/180; 427/185; 424/490; 424/495

(58) Field of Classification Search
USPC ........................................ 427/2.15
See application file for complete search history.

(56) References Cited

U.S. PATENT DOCUMENTS

| | | | |
|---|---|---|---|
| 5,552,152 A | 9/1996 | Shen | |
| 6,475,523 B1 | 11/2002 | Staniforth | |
| 6,740,341 B1 * | 5/2004 | Holt et al. | 424/490 |
| 7,276,249 B2 | 10/2007 | Ryde et al. | |
| 8,252,370 B1 | 8/2012 | Young et al. | |
| 2002/0098227 A1 | 7/2002 | Nouri et al. | |
| 2004/0137156 A1 * | 7/2004 | Lee et al. | 427/385.5 |
| 2008/0179433 A1 * | 7/2008 | Pfeffer et al. | 241/5 |
| 2009/0269411 A1 * | 10/2009 | Bellinghausen et al. | 424/490 |
| 2011/0003006 A1 * | 1/2011 | Venkatesh et al. | 424/495 |

FOREIGN PATENT DOCUMENTS

EP    2201939 A1    6/2010

OTHER PUBLICATIONS

Yang J, et al., "Dry Particle Coating for Improving the Flowability of Cohesive Powders". Powder Technology, V. 158, 2005, pp. 21-22.
Chen Y, et al., "Fluidization of Coated Group C Powders"; AIChE Journal, V. 54, 2008, pp. 104-121.

(Continued)

*Primary Examiner* — Cachet Sellman
(74) *Attorney, Agent, or Firm* — Mendelsohn, Drucker & Dunleavy, P.C.

(57) ABSTRACT

A taste masked particulate pharmaceutical formulation include a core that comprises an active pharmaceutical ingredient; at least a partial nanoparticle material layer on the core that comprises a nanoparticle material with a median particle size not greater than 100 nm; a first polymer layer that is at least partially water soluble and a second polymer layer that is water insoluble. The active pharmaceutical ingredient is completely released in 30 minutes in the USP Dissolution Test. A process of making the particulate pharmaceutical formulation using sequential fluidized bed coating steps under controlled conditions is also described.

13 Claims, 15 Drawing Sheets

(56) References Cited

OTHER PUBLICATIONS

Chen Y, et al., "Fluidized Bed Film Coating of Cohesive Geldart Group C Gowders" Powder Technology. v189 (2009) pp. 466-480.
Han, X. et al., "Simultaneous Micronization and Surface Modification for Improvement of Flow and Dissolution of Drug Particles" International Journal of Pharmaceutics, 2011. 415(1-2): p. 185-195.
Pfeffer, R. et al., "Synthesis of Engineered Particulates With Tailored Properties Using Dry Particle Coating," Powder Technology, vol. 117, pp. 40-67, 2001.
Yang, J. et al.,"Dry Particle Coating for Improving the Flowability of Cohesive Powders." Powder Technology, 158, 2005, 21-33.
International Search Report and Written Opinion; Mailed Jan. 3, 2014 for the corresponding PCT Application No. PCT/US2013/064064.

* cited by examiner

TASTE MASKED ACTIVE PHARMACEUTICAL POWDER COMPOSITIONS AND PROCESSES FOR MAKING THEM

BACKGROUND OF THE INVENTION

1. Field of the Invention

The present invention relates to taste masking of active pharmaceutical ingredients. In particular, it is directed to a particulate pharmaceutical formulation taste masked with a bi-layer coating and a process of producing the same.

2. Description of the Related Technology

Medication compliance is a significant challenge for patients who have difficulties swallowing, such as young children, the very elderly and patients with dysphagia. The pharmaceutical industry has developed a number of drug delivery protocols to address this challenge, including rapid in-mouth disintegrating tablets, tablets which disintegrate in liquid prior to ingestion, liquids and syrups, gums and even transdermal patches. Unfortunately, each of these methods has its own problems. For example, transdermal patches can be inconvenient or uncomfortable to use and quite expensive to produce. The flux of drug through the skin can also raise complex dosing issues.

U.S. Pat. No. 6,740,341 discloses that masking the bad taste of an active pharmaceutical ingredient (API) can make it pleasant enough to chew and swallow, therefore making it easier for patients to ingest the medication. A variety of methods have been used to mask the taste of an API. These include the use of flavorings, sweeteners, effervescent systems and various coating strategies. One particularly effective method is microencapsulating API powders by coating with ethyl cellulose, a mixture of ethyl cellulose and hydroxypropyl cellulose, or other cellulose derivatives, to provide chewable taste-masked medications. U.S. Pat. No. 6,740,341 also discloses a taste masking formulation that includes a taste masking layer and a spacing layer over the drug particles. The drug particle sizes may be up to 1500 μm, which can introduce an undesirable gritty feeling for orodispersible dosage forms. Additionally, this formulation requires two layers of at least 5 μm thick, leading to a high polymer loading, which may affect the size of the dosage form.

U.S. Pat. No. 5,552,152 discloses a chewable taste-masked tablet having controlled release characteristics comprising microcapsules of from about 100 μm to about 0.8 mm in diameter. The microcapsules have a pharmaceutical core of crystalline ibuprofen and a methacrylic acid copolymer coating with sufficient elasticity to withstand chewing. Large microcapsule sizes are preferred (0.25-1 mm in diameter), because larger microcapsules are easier to manufacture and package, and less expensive to produce than smaller microcapsules. However, microcapsules of this size may fracture during chewing and release drug from the microcapsule, especially when there is an inadequate amount of plasticizer or other component included to provide sufficient elasticity. Therefore, larger sized microcapsules require greater elasticity to minimize the likelihood of fracturing during chewing.

Yang et al. discloses several processing techniques for dry coating cohesive corn starch powder with different silica particles (Yang J, Sliva A, Banerjee A, Dave, RN, Pfeffer R. Dry particle coating for improving the flowability of cohesive powders. Powder Technology, V. 158, 2005, 21-22). The nanosized silica particles provide good flowability enhancement, as compared with mono-dispersed 500 nm silica. It further taught that surface-treated hydrophobic silica is more effective in improving the flowability of corn starch particles than untreated hydrophilic silica. However, Yang et al. is only concerned with flowability and not taste masking.

Chen et al. discloses a process to deposit a very small amount of nano-sized particles (as low as 0.01% by weight) with a high degree of precision onto the surface of cohesive powders, Geldart group C powders (Chen Y, Yang J, Dave R N, Pfeffer R. Fluidization of Coated Group C Powders. AIChE Journal, V. 54, 2008, 104-121). The process improves the flowability and fluidizability of cohesive powders. Chen et al. only discusses the fluidization behavior of ideal cohesive powders such as corn starch, which is often added to pharmaceutical formulations. Chen et al. does not discuss fluidizing active pharmaceutical ingredients, which typically have irregular shapes, high surface energy, and undergo significant tribocharging. Another publication from Chen et al. discloses a process of using fluidized bed film technology to coat group C powders that are deposited with nanosize silica particles on their surface (Chen Y, Yang J, Mujumdar A, Dave, R N. Fluidized bed film coating of cohesive Geldart group C powders. Powder Technology. v189 (2009) 466-480). The examples disclosed in this paper are limited to substantially spherical cornstarch and aluminum particles.

U.S. Pat. No. 7,276,249 discloses a composition including a fibrate, preferably fenofibrate, and at least one surface stabilizer adsorbed on the surface of the fibrate particles. The fibrate particles have an effective average particle size of less than about 2000 nm.

A significant issue for prior art processes is agglomeration of API particles in traditional fluidized bed coating processes, which typically leads to particle sizes much larger than 100 μm and results in an unpleasant gritty mouth feel that make these dosages unpalatable. The present invention provides a process to produce taste masked API powders by fluidized bed coating with minimal agglomeration of drug particles. The process of present invention also requires a lower polymer loading to allow for API's having a relatively high potency.

SUMMARY OF THE INVENTION

In a first aspect, the present invention is directed to a particulate pharmaceutical formulation comprising: a core including an active pharmaceutical ingredient; a nanoparticle material on the core including nanoparticle material with a median particle size not greater than 100 nm; a first polymer layer that is at least partially water soluble; and a second polymer layer that is water insoluble. The core is covered by the nanoparticles on its surface with a surface area coverage of 30% to 100%. The taste of the active pharmaceutical ingredient is at least partially taste masked when ingested in the particulate pharmaceutical formulation, relative to uncoated active pharmaceutical ingredient. In this particulate pharmaceutical formulation the active pharmaceutical ingredient is completely released in 30 minutes in the USP Dissolution Test.

Another aspect of the present invention is directed to a process for preparing a particulate pharmaceutical formulation from core particles that comprises an active pharmaceutical ingredient and a nanoparticle coating with nanoparticles that have a median particle size not greater than 100 nm. The process includes the steps of: coating the core particles with a first polymer layer by spraying a first polymer solution onto the core particles in a fluidized bed to form a first polymer coating; and coating the core particles coated with the first polymer with a second polymer on the first polymer coating by spraying a second polymer solution to the core particle coated with the first polymer in a fluidized bed. The first polymer layer is at least partially water soluble. The second polymer layer is water insoluble and is capable of at least partially taste masking the active pharmaceutical ingredient.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In a first aspect, the present invention relates to a process for making a taste masked powder preferably containing an active pharmaceutical ingredient (API).

Figure 1:
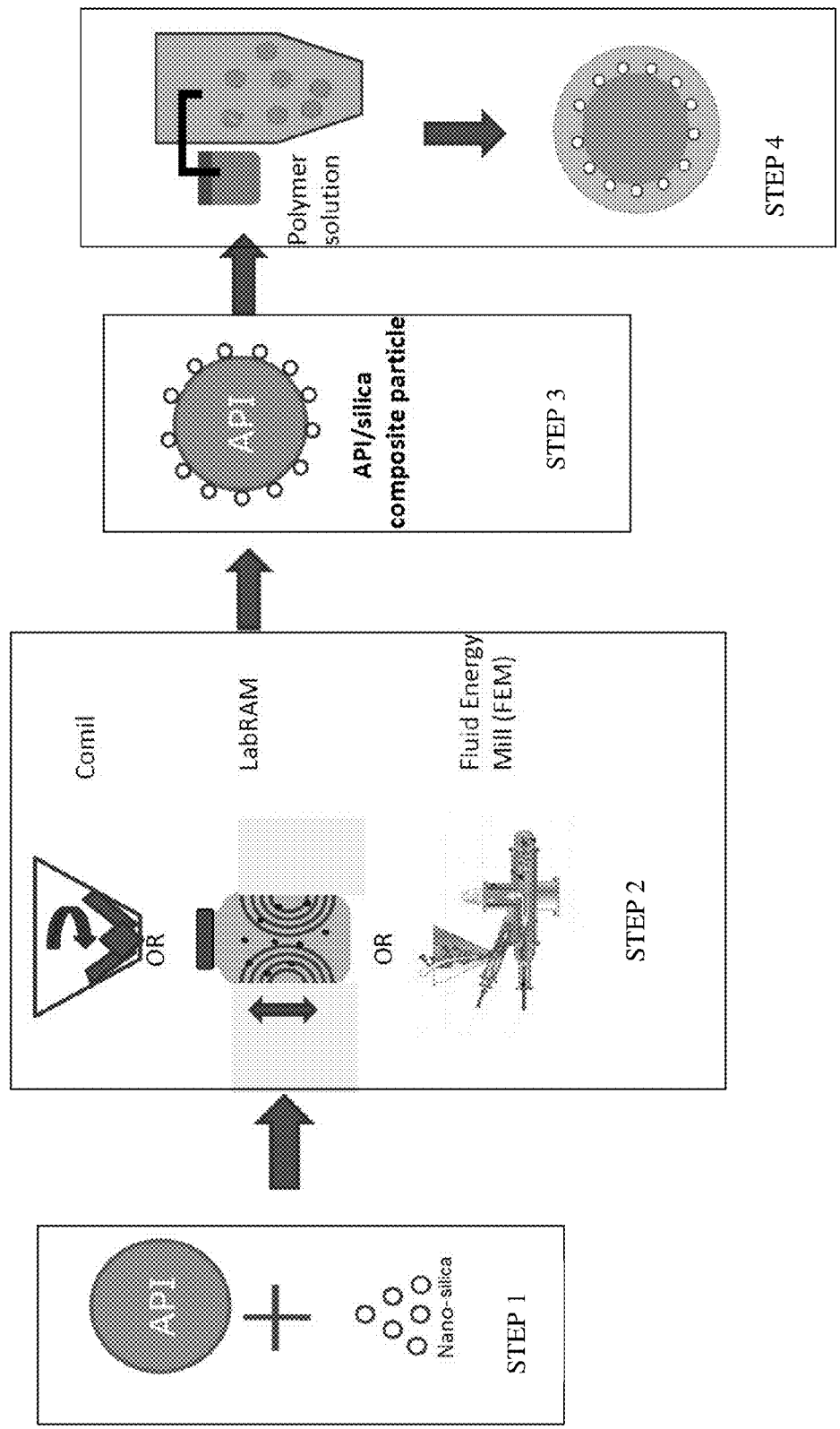
FIG. 1 is a schematic representation of fluidized bed coating process according to some embodiments of the present invention.

An exemplary process is depicted in FIG. 1. The exemplary process of FIG. 1 employs API powder and silica particles. The API powder is a core particle comprising an active pharmaceutical ingredient (API) that has an undesirable taste. The API core particles have a much larger particle size than the silica particles. The API core particles may, for example, have a volume averaged median particle size in the range from 1 µm to 200 µm, in the range from 5 µm to 150 µm, or in the range from 10 µm to 100 µm. The API core particles may consist of a plurality of particles with a narrow particle size distribution because API core particles with wider size distributions that include both fine and coarse particles are more likely to agglomerate during mixing and coating.

A person skilled in the art can select an acceptable size range based on the width of the size distribution, which may be specified in terms of its span, defined as (d90−d10)/d50. Here, d90 indicates the size below which 90 percent volumetric distribution resides, and likewise, d50 is the median of the volumetric size distribution and d10 is the size below which 10 percent volumetric distribution resides. The span should be less than about 3, more preferably less than about 2. A span of up to 4 may also be acceptable, provided that the fines or coarse fractions do not have very long-tailed distributions. Preferably the d90 particle sizes are less than 300 µm and the d10 particle sizes are greater than 25 µm.

Although silica has been used in the exemplary embodiment of FIG. 1, the present invention may employ any type of nanoparticles that have relatively low dispersive surface energy of less than 60 mJ/m$^2$ preferably less than 40 mJ/m$^2$ and a median particle size of from 5 nm to 100 nm to coat the API core particles. Preferably, the nanoparticles comprise one or more materials that are on the United States Food and Drug Administration's list of GRAS (generally regarded as safe) materials and are cleared for internal and/or pharmaceutical use. Examples of nanoparticle materials include nanoparticles of silica, alumina, titania, carbon black, aluminum calcium silicate, calcium silicate, magnesium silicate, potassium silicate, sodium silicate, sodium aluminosilicate, sodium calcium aluminosilicate, tricalcium silicate, silica aerogel, talc, iron oxide, other metal oxides and mixtures thereof. The nanoparticle may have a particle size in the range of 1-30 nm or 7-15 nm, and should have a dispersive surface energy low enough in relation to the surface energy of the API core particles so that the nanoparticles can be deagglomerated and easily spread/coated over the API core particles. Such a coating leads to reduced cohesion of the carrier particles, which in this case are fine pharmaceutical drug particles. Such fine carrier particles are usually cohesive and cannot be fluidized. While the most reliable way to test if a particle can be fluidized or not is by actually trying to fluidize it, indirect indications of improved fluidizability may also be gathered through reduced Angle of Repose (AoR) or increased flow function coefficient (FFC). Any GRAS nano-particles that sufficiently reduce AoR or increase FFC and subsequently show improved fluidization when they are subjected to fluidizing gas are acceptable as coating materials in the present invention.

It is expected that the original fine drug powders may have an AoR of greater than 50 degrees or even 55 degrees and an FFC of 5 or less, or 3 or less when measured in with the appropriate powder characterization equipment by a person skilled in the art. Coating with nano-particles may change the powder flow properties and the AoR is expected to be less than 45 degrees and more preferably less than 40 degrees or even lower, while the FFC may increase to 6 or even higher, for example greater than 8.

As an illustrative example, ibuprofen powder having median particle size of about 74 micron was considered. Before coating, it had an AoR of about 55 degrees (measured in a Hosokawa Powder Tester, PT-N, Hosokawa Micron, Japan, as per the ASTM standard ASTM D6393-08), and an FFC of about 5 as measured in a shear cell of FT 4 tester (Freeman Technologies, UK) under pre-consolidation of 3 kPa based on the recommendation of 205 ASTM standard for powders having low density (Emery et al., 2009; Emery, E., Oliver, J., Pugsley, T., Sharma, J., Zhou, J., 2009, "Flowability of moist 688 pharmaceutical powders," Powder Technol. 189, 689 409-415) and the range normally used for pharmaceutical powders. After dry coating ibuprofen with 2 wt % R972p nano-silica, the AoR was reduced to about 39 degrees, while the FFC increased to over 10; both indicating substantial flow improvement and thus implying a reduction in cohesion as may be recognized by those skill in the art. As an another example, even finer ibuprofen powder of median size of about 41 micron had an AoR of about 58 degrees and FFC of about 2.8, and after dry coating with 2 wt % R972p nano-silica, the AoR was reduced to about 37 degrees, while the FFC increased to over 10. Both of these ibuprofen powders could not be fluidized sufficiently prior to coating, yet both of the coated ibuprofen particles were well fluidized after dry coating.

Fluidization of otherwise not fluidizable pharmaceutical powders is due to reduced cohesion upon dry coating based surface modification. In general, there are two factors that contribute to the inter-particle attraction, hence cohesion of such powders. The first factor is the material surface property generally represented by its surface energy or by the Hamaker constant. In general, a lower Hamaker constant or lower dispersive component of surface energy will lead to reduced inter-particle attraction, all else being equal, and thus reduced cohesion.

The second factor is also a surface property, and it is the roughness at the contact surface between two particles. With all else being equal, either very rough, i.e., roughness on the order of 100 nm or higher, or very smooth, i.e., atomic smoothness or roughness of less than a few nm, e.g., 5 nm, have higher inter-particle attraction than those which may be called nano-rough; i.e., having a surface roughness between 5 to 100 nm, for example measured using an Atomic Force Microscope. More preferably, a surface roughness between 7-30 nm is employed. Dry coating with nano-silica or other acceptable GRAS particles having a particle size of 5-100 nm, and more preferably a particle size of 10-25, can thus lead to reduced cohesion due to imparted nano-scale surface roughness. There could be an additional effect of cohesion reduction if the dispersive component of surface energy of the nano-particle is in general low (<60 mJ/m$^2$, preferably <40 mJ/m$^2$), or alternately less than the original pharmaceutical powder.

Since cohesion reduction could occur due to one or both of factors listed above, in lieu of coating using nanoparticles, softer, deformable materials that have flaky nature and smear upon mixing may also be used. Such coatings also result in a low dispersive surface energy of the coated product. Thus coating may be also done with materials such as; magnesium stearate, stearic acid, leucin, amino acids, and other materials typically used in inhalation applications to impart dispersion through hydrophobic and/or low adhesion materials; see for example U.S. Pat. No. 6,475,523 that contains a comprehensive list of surface active molecules, the disclosure of which is hereby incorporated by reference. Thus such materials would replace silica or nano-sized, discrete particles with deformable/flaky materials. The reduction in cohesion occurs due to lower dispersive surface energy and could also be due to reduced surface roughness as a result of a softer material filling in voids in a rough surface resulting in a smoother surface.

As per the discussion above, coating with nanoparticles having a particle size near the lower end of the range produces a greater improvement of the fluidization of the API powders. However, when the median particle size of the nanoparticles is smaller than 5 nm, the improvement in fluidization may be reduced.

The silica particles used in the present invention may be of any type, such as hydrophobic treated silica or fumed silica. Examples of suitable silicas include Aerosil R972 silica (Evonik), CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 200 VV Pharma (Evonik), AEROPERL® 300 Pharma (Evonik), OX-50 silica (Evonik), COSMO55 (Catalyst & Chemical Ind. Co. Ltd (Japan)), P-500 hydrophilic silica (Catalyst & Chemical Ind. Co. Ltd (Japan)) and TS530 silica (Cabot). In general, preferred are the fumed amorphous silicas with a specific surface area of greater than about 100 $m^2/g$. Typically, these fumed amorphous silicas are produced via gas-phase synthesis and undergo surface modification to alter their hydrophobicity. In some embodiments, more than one type of silica may be used in combination. For example, silica TS5 and silica R972 may be used together.

Hydrophilic silica may be obtained by hydrophobic treatment to make the silica hydrophobic. In one embodiment, the hydrophobic treatment of hydrophilic silica may be accomplished by treating the hydrophilic silica with dichlorodimethanolsilane. Any other suitable methods known to a skilled person that are capable of modifying silica to hydrophobic silica may be used. Hydrophobic silica, in addition to improving flow and fluidization properties, may aid in delaying the wetting of the coated API and delaying its initial release.

The weight amount of the silica to be coated onto the API powder is in the range from 0.1 to 10% by weight of the total weight of the API powder and silica. Alternatively, from 1 to 5% by weight of silica may be employed. It is believed that using high concentrations of silica (i.e. much greater than 100% surface area coverage (SAC)) could dry coat the API and also leave silica particles available during the fluid bed coating process. This excess silica is available to dislodge from the composite and dry coat the polymer coated powder during the subsequent fluid bed coating process.

Referring to FIG. 1, the API powder and nano-silica are provided at step 1. At step 2 the API powder is mixed with the silica in a manner which dry coats the API powder with silica to produce API-silica composite particles. The purpose of the dry coating step is to enhance the fluidization and minimize agglomeration of the coated API powder.

Apparatus for performing the dry coating step 2 may be any suitable apparatus known to a skilled person. Suitable apparatus include, but not limited to, a Comil (U3 Quadro Comil of Quadro Pa., U.S.), a LabRAM (Resodyne Minnesota, U.S.), a Magnetically Assisted Impact Coater (MAIC, Aveka Minn., U.S.) and a Fluid Energy Mill (FEM, Qualification Micronizer of Sturtevant Mass. U.S.). Other examples of dry coating devices include, the Hybridizer or Omnitex (Nara Machinary, Tokyo, Japan), the Mechanofusion or more recent versions such as Nobilta and Nanocular (Hosokawa Micron Powder Systems, Osaka, Japan), the Theta composer (Tokuju Corporation, Tokyo, Japan), and to some extent, any high intensity mixers, for example, the V-blender with agitation bar (PK Blend Master® Lab Blender, Patterson-Kelly, East Stroudsburg, Pa.) and (Cyclomix, Hosokawa Micron Powder Systems, Osaka, Japan). The FEM is able to simultaneously mill and dry coat the API powders to achieve coated API particle sizes that are equal to or less than 50% of the initial API powder particle size. Dry coating of the API powders can be accomplished in a relatively short time in the devices designed to perform dry coating. In contrast, some of the low intensity mixers may be used but require longer processing times. In all cases, larger scale devices would provide larger production rates without significantly changing the processing times. A person skilled in art would be able to develop a suitable scale-up strategy.

Figure 3:
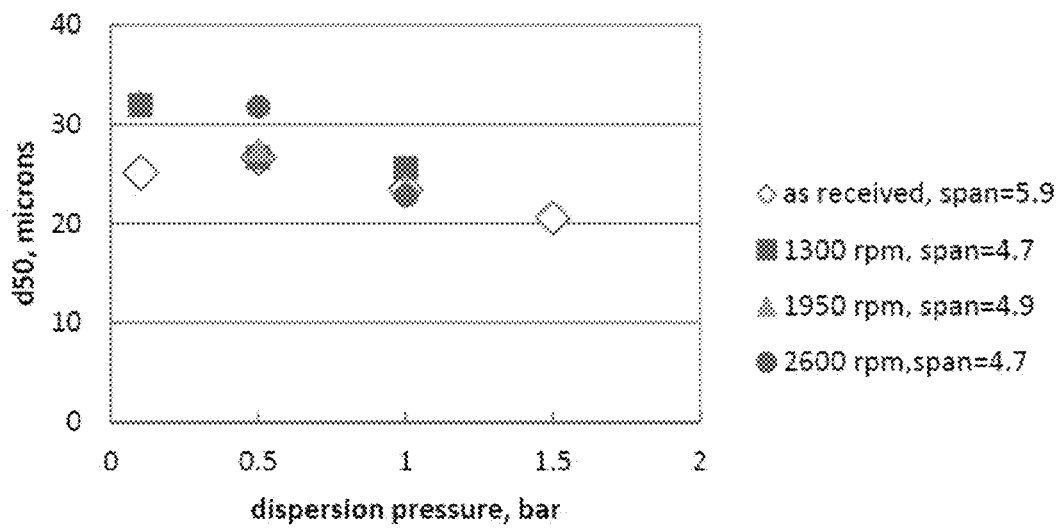
FIG. 3 depicts the effects of impeller speed on agglomeration.

The operating conditions for coating step 2 may be established by a skilled person giving consideration, for example, to particle agglomeration and providing reduced angle of repose (AOR) values for the coated API powder. The degree of particle agglomeration may be determined by measuring the size of the coated particles in SEM images. The degree of agglomeration may also be estimated using the dispersion pressure titration in the Rodos/Helos system (Rodos and Helos, Sympatec, Lawrenceville, N.J., USA). A discussion of the pressure titration may be found in Han, X., Ghoroi, C., To, D., Chen, Y., Davë, R., "Simultaneous micronization and surface modification for improvement of flow and dissolution of drug particles (2011)." *International Journal of Pharmaceutics*, vol. 415, pp. 185-195, which is incorporated in its entirety by reference. The AOR may be measured using the procedure of ASTM D6393-99, "Bulk Solids Characterization by CARR Indices." For example, when the Comil is used, the impeller speed may be optimized to reduce the agglomeration (FIG. 3) as higher impeller speed increases agglomerate size for the silica coated API powders.

The product after dry coating the API powder with silica is depicted in step 3. These silica coated API powders are referred to as "API-silica composite particles." The silica particles, preferably hydrophobic, on the surface of the API-silica composite particles help to minimize agglomeration by introducing modified surface properties in the form of a nano-sized surface asperity and modified surface energy. Additionally the introduction of hydrophobic silica can potentially slow the dissolution of the API-silica composite particles. Though the API powders are often cohesive, the API-silica composite particles have good flow properties and are fluidizable.

The surface area coverage (SAC) of the API powders with silica may be estimated by image analysis of SEM images of the API-silica composite particles. In some embodiments, the SAC of the API-silica composite particles is in the range of from 15% to 100%, in the range of from 25% to 100%, or in the range of from 35% to 100%. In some embodiments, the SAC may be proximate to 100%.

The API-silica composite particles are the feed to step 4 of FIG. 1, which is a fluidized bed coating process. The fluidized bed coating process of step 4 is employed to coat the API-silica composite particles with first and second polymer layers to produce bi-layer coating which taste masks the API. The first polymer layer (inner coating) is at least partially water soluble. The second polymer layer (outer coating) is completely water insoluble.

The final taste masked product after the fluidized bed coating process has a core that comprises an active pharmaceutical ingredient, silica particles on the core, a first polymer layer that is at least partially water soluble, and a second polymer layer that is water insoluble.

Figure 2:
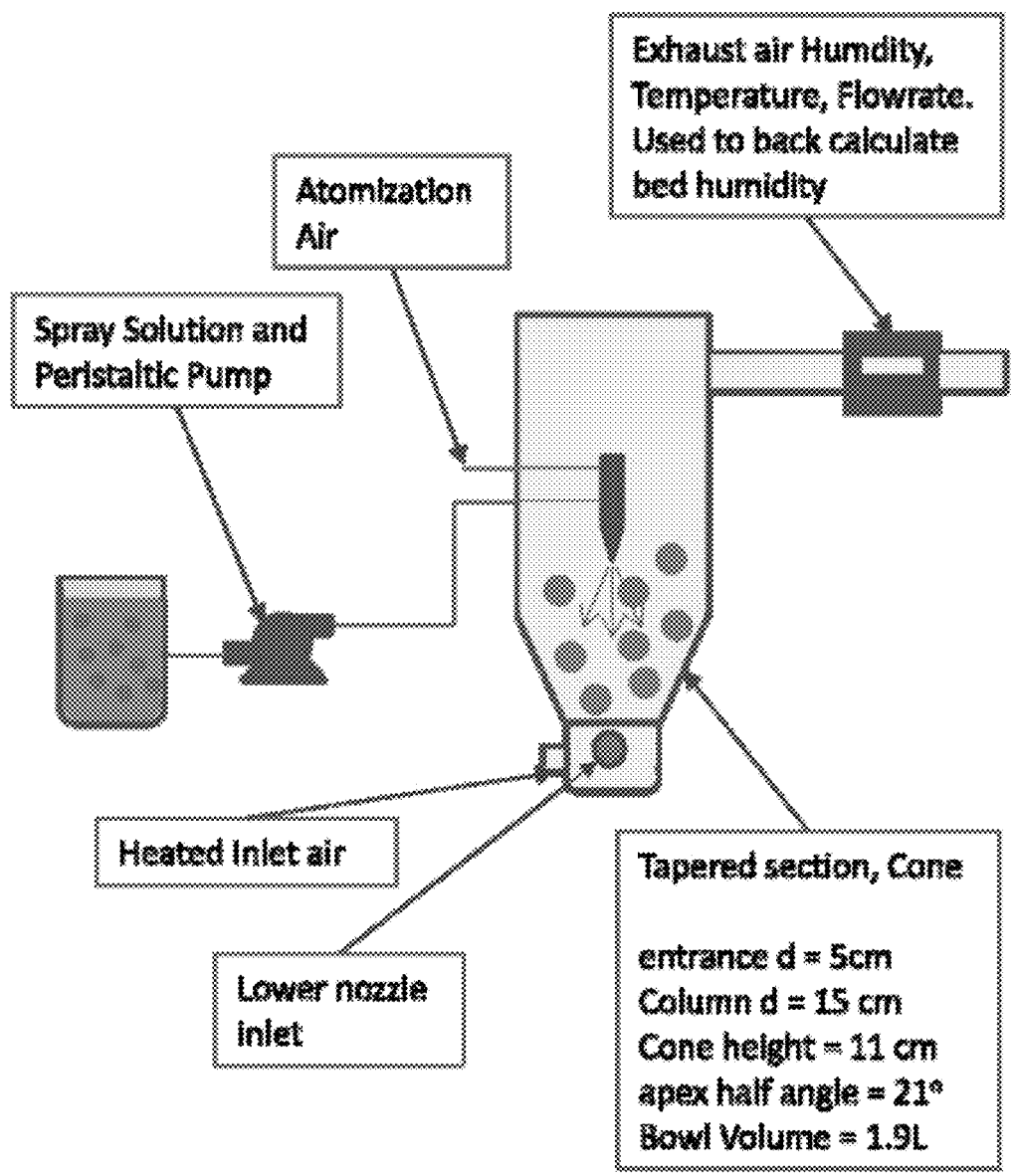
FIG. 2 is a schematic representation of the Mini-Glatt 9550 that may be used in the present invention.

In the fluidized bed coating process 4 of FIG. 1, the API-silica composite particles are fed to the fluidized bed coating chamber. Heated air is blown into the chamber to circulate the particles in the chamber. A first polymer solution is then pumped to a nozzle, which sprays atomized polymer solution into the fluidized bed coating chamber. A second polymer solution may then be pumped to the nozzle and sprayed into the fluidized bed coating chamber. The fluidized bed coating may be accomplished through top spray coating, bottom spray coating, tangential spray coating, or any other suitable method. A Mini-Glatt 9550, manufactured by Glatt of New Jersey, U.S. may be used as a suitable apparatus for the fluidized bed coating process. A Mini-Glatt 9550 is shown in FIG. 2 configured for top-spray fluidized bed coating.

Both the first polymer solution and the second polymer solution are each sprayed into the fluidized bed coating chamber, after being atomized, as fine droplets. The fine droplets attach to the surface of API-silica composite particles and form a polymer layer after the solvent of the polymer solution droplets is evaporated.

The first polymer solution of the present invention comprises at least one water soluble polymer or partially water soluble polymer. The first polymer layer on the API-silica composite particles is thus water soluble, or contains water insoluble polymer with an appropriate amount of water soluble materials to allow dissolution of the active material with only a small delay of less than 15 minutes in an appropriate dissolution media such as phosphate buffer solution with a pH of 7.2. The water soluble polymer has a solubility of at least 50 mg/ml of polymer in water at neutral pH and room temperature, while the insoluble polymer has a solubility of at most 0.001 mg/ml of polymer in water, at a range of pH from 6 to 7.2, and at room temperature to about 37° C.

Multiple polymers may be present in the first polymer solution. Examples of suitable polymers for the first polymer layer include hydroxypropyl methylcellulose (HPMC), hydroxypropyl cellulose (HPC), polyvinylpyrrolidone (PVP), polyvinyl alcohol (PVA), ammonio methacrylate copolymer, ethylcellulose and combinations thereof. In one exemplary embodiment, a first layer of polymer that contains 45% HPMC and 55% ammonio methacrylate copolymer is employed. When the polymer in the first polymer solution is water soluble, the solvent is preferably water. However, when the polymer is only partially water soluble, another solvent such as a mixed solvent including water and one or more organic solvents may be used. One example of a suitable solvent is a water and ethanol mixture. The first partially soluble polymer layer is used to separate a second insoluble polymer layer from the drug and to offer fast release of the API. Additionally, the first partially soluble layer introduces controlled agglomeration, which can be effective at minimizing defluidization during the fluidization of the second polymer layer.

The polymer loading of the first polymer layer may be up to about 20 wt. %, or in the range of from 2 wt. % to 15 wt. %, or in the range of from 5 wt. % to 10 wt. % of the total weight of the final taste masked product including the second polymer layer. The thickness of the first polymer layer on the API-silica composite particles may be between 0.5 µm and 5 µm, more preferably between 1 µm and 3 µm.

In some embodiments it may be desirable to employ silica, which may be stabilized silica, in the first polymer solution. The silica in the first polymer solution is employed to reduce or prevent agglomeration during the fluidized bed coating process. Silica suitable for this purpose may have a median particle size in the range of from 100 nm to 500 nm, and is preferably amorphous colloidal silica. Silica particles with a diameter of 180 nm or larger can be prepared by using the well-known the Stöber process (see e.g. "Controlled growth of monodisperse silica spheres in the micron size range," *Journal of Colloid and Interface Science*, Volume 26, Issue 1, January 1968, Pages 62-69, Werner Stöber, Arthur Fink, Ernst Bohn doi:10.1016/0021-9797(68) 90272-5). This second silica is different from the first silica used for dry coating the API powders, which has a smaller median particle size (less than 100 nm, more preferably less than 25 nm). The silica is preferably stabilized against aggregation. Conventional techniques may be used to stabilize the silica particles, including increasing ionic strength with NaOH, or by adjusting the pH of the silica solution.

The amount of this second silica in the first polymer solution depends on the polymer and solvent used. In one embodiment, the first polymer solution includes silica dispersed in a sodium hydroxide solution, with an amount of silica of up to about 1 to 10% by weight of total polymer suspension.

The first polymer layer is at least partially water soluble. This first polymer layer can completely cover the API-silica particles without resulting in significant agglomeration of the particles. Additionally the first polymer layer may help prevent severe defluidization during the coating of the second polymer layer. This first polymer layer may be employed to control some of the dissolution characteristics of these taste masked medications.

The second polymer layer is a water insoluble but permeable layer, which will slow down the release of the API from the taste masked particles. The second polymer solution comprises at least one polymer that is water insoluble. Suitable polymers for the second polymer layer include Eudragit RS 100, ammonio methacrylate copolymer, ethylcellulose, and combinations thereof. The second polymer layer masks the taste of the API in the taste masked particles thereby providing a reduction or elimination of an undesirable taste characteristic of the API.

The second polymer solution preferably employs an organic solvent, such as ethanol, acetone, and solvents that are mixtures of organic and inorganic solvents. The selection of organic solvents should be limited to those that are approved for use in food manufacture.

The polymer loading of the second polymer layer may be up to 25 wt. %, or in the range of from 2 wt. % to 15 wt. %, or in the range of from 5 wt. % to 10 wt. % of the final taste masked product. The thickness of the second polymer layer may be between 0.5 µm and 5 µm, or between 1 µm and 3 µm. The combined thickness of both the first polymer layer and the second polymer layer may be between 2 µm and 10 µm, or between 3 µm and 6 µm.

In some embodiments, the spray of the second polymer solution may be preferably blended periodically with small amounts of silica to reduce cohesion therefore minimizing the chance of particles sticking to the wall or undesirable agglomeration of the particles. One embodiment employs the addition of silica to provide a 0.1-1.0% weight gain for every 2% of weight gain of the polymer coated.

The silica that may be used for blending with the spray of the second polymer solution may be the same silicas discussed above for blending with the first polymer solution. One suitable silica is Aerosil R972P (or pharmaceutical grade R972P), and other examples include, CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 200 VV Pharma (Evonik), AEROPERL® 300 Pharma (Evonik).

The droplet size of the sprayed polymer solutions is important for the fluidized bed coating performance and final taste masking properties. Larger droplet size may create difficulties in drying and subsequently lead to the formation of undesired agglomerates. On the other hand, smaller droplet sizes may result in the loss of polymer material due to rapid evaporation of solvent before the droplets reach the surface of the particles. The droplet size of a sprayed polymer solution may be measured using the Malvern Spraytec system (Malvern Instrument Inc., UK) on a nozzle with orifice of 0.5 mm, located at a distance of 15 cm from the laser beam and at a position of 15 cm from the focal lens. A skilled person can determine a suitable droplet size for the spraying of the polymer solutions.

The droplet size of the sprayed polymer solution may be influenced by the polymer concentration in the solutions. The mean droplet size increases nonlinearly with the polymer concentration, because highly concentrated polymer solutions tend to be highly viscous and require more energy in order to be atomized into fine droplets. Thus, polymer solution with high polymer concentration (thus higher viscosity) may require higher input energy to atomize the solution to produce small-sized droplets.

The preferred droplet size is less than the size of the API-silica composite particles. In some embodiments, the preferred droplet size is in the range from 5 µm to 15 µm, or in the range from 7 µm to 12 µm. Also, in some embodiments it may be advantageous to ensure that the droplets of the sprayed polymer solutions have narrow droplet size distributions, to encourage homogenous polymer film formation. It is preferred that the ratio of the d90–d10 and the d50 is equal to or less than 2. A wider distribution could result in spray drying of the fine fraction, while the coarse fraction could promote agglomeration.

The spray rate for spraying both the first polymer solution and second polymer solution may also influence the fluidized bed coating performance. Lower polymer concentrations in the polymer solution may allow use of a higher spray rate. The spray rate, however, must be balanced with the fluidizing velocity. The fluidizing velocity can be chosen such that the powder can be adequately fluidized. High spray rates can lead to humid conditions that can induce agglomeration, while low spray rates can lead to dry conditions that induce spray drying. The spray rate may be correlated with the droplet size distribution, where the droplet size distribution typically varies linearly with spray rate and is inversely proportional to the square of the pressure.

A suitable fluidization velocity in a Mini-glatt apparatus for reducing agglomeration during fluidized bed coating from 1 cm/s to 10 cm/s, or preferably 3 to 7 cm/s. The spray rate should be controlled such that the environmental conditions inside the fluidized bed are within the limits of 25-40% RH and 25-30° C.

Depending on the scale of the fluidized bed the fluidization flow rate (the product of the superficial gas velocity and cross-sectional area of the bed), the spray rate and the atomization pressure can be controlled to keep the superficial gas velocity and droplet size distribution within desired limits, while still keeping the environmental conditions inside the bed within desired limits.

Fine API powders such as fine ibuprofen powders, may require lower fluidizing velocities than unmilled, coarse ibuprofen particles. This lowers the fluidizing flow rate that can be used during fluidized bed coating. Additionally, the spray rate will may have to be lowered to compensate for the change in gas velocity. Ultimately this can lead to significantly longer processing times, which is shown in Table 1 for milled powders (41 μm) and unmilled powders (74 μm). While these processing times are long, they are reasonable considering there are few feasible alternative approaches to coat finer, milled powders.

TABLE 1

Fluidized bed coating conditions for milled and unmilled ibuprofen powders

|  | 41 μm | 74 μm |
| --- | --- | --- |
| Fluidizing velocity (cm/s) | 0.7 | 1.6 |
| Fluidizing flowrate (cfm) | 2.1 | 4.3 |
| Sprayrate (mL/min) | 0.61 | 1.26 |
| Time (hours) to achieve 10% under layer | 13 | 7 |

In some embodiments, spraying of the first polymer solution, the second polymer solution, or both may be accomplished using an intermittent spray technique. Intermittent spraying is achieved by periodically spraying the polymer solution for a set interval and then discontinuing spraying for a set interval in which time some drying will occur. One suitable intermittent spraying cycle may employ a 120 second spraying period and a 120 seconds non-spraying period. Other suitable spraying periods may range from 20 seconds to 3 minutes with non-spraying periods also ranging from 20 seconds to 3 minutes, without requiring that both the spraying and non-spraying periods are the same.

The process of the present invention can be used to produce taste masked API containing particles wherein an undesirable taste characteristic of the API is reduced or eliminated. Polymer loading for the combined polymer layers may be less than 20% by weight, based on the total weight of the taste masked particles. These polymer loadings are substantially lower than those employed for many prior art taste masking applications, due to the minimized particle agglomeration, while still achieving high quality, uniform coatings that impart the desired taste masking attribute.

The final taste masked product may have significant problems of adhesion and caking during storage. To prevent these problems, the present invention may comprise a further step of coating the taste masked product with silica. This further step may be used to dry coat the taste masked particles with up to 2%, or about 0.5-1.5% by weight of silica particles, based on the total weight of the silica coated taste masked product. These silica particles are preferably smaller than 100 nm. One suitable silica is Aerosil R972 which can be used to produce a well flowing taste masked powder. Other silicas that may be used include, CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 200 VV Pharma (Evonik), AEROPERL® 300 Pharma (Evonik). This silica coating step may be accomplished, for example, with LabRAM at 50 G's for 30 seconds or by simply blending the taste masked particles with the silica particles.

The taste masked product substantially prevents or completely prevents release of the API of the product while being chewed, therefore masking its taste during chewing. A panel of persons may be used to assess the degree of taste masking, as is the common practice in the pharmaceutical industry. The polymer coatings do not significantly alter the dissolution behavior of the API core particles. The two polymer layers are capable of quickly releasing the API in the digestive tract. A dissolution test may be used to assess the speed of release of the API from the product. The taste masked particles of the present invention may completely release the API within 30 minutes in a USP Dissolution Test, or within 20 minutes or within 15 minutes in a USP Dissolution Test.

The present invention uses a USP Dissolution Test to assess the release of API from the final product, which test is performed with a media of 7.2 pH phosphate buffer solution with 0.4 g/L sodium dodecyl sulfate (SDS) used to ensure wetting of the powders, at 37° C. and USP Apparatus II (paddles) rotating at 50 RPM. The percentage of active pharmaceutical ingredient that is dissolved is measured over time.

EXAMPLES

Example 1

Ibuprofen powder with a median core particle size of 74 μm (IBU50, manufactured by BASF) was dry coated with silica using a Comil. 588 g of IBU50 powder was preblended with 12 g of Aerosil R972 hydrophobic silica (2% loading, manufactured by Evonik Degussa) in a V-blender (Patterson Kelly) at 27 RPM for 5 minutes and 15 seconds. The powder was then fed into the Comil using a calibrated screw feeder at a flow rate of 10 g/min. The Comil was fitted with a 457 μm conical screen and a rounded impeller was operated at 1300 RPM (this impeller speed was achieved by reducing the minimum operating frequency to 16.8 Hz). A special processing cycle was used to compensate for the low impeller speed. With the impeller on, the powder was fed for 10 minutes. The impeller remained on for an additional 5 minutes without feeding powder. The impeller was then stopped for 5 minutes, to prevent overheating. After the instrument was cooled down, the impeller was started again, followed by continuing the feeding of the IBU50 powder.

Example 2

Ibuprofen IBU50 was dry coated with silica using a LabRAM. A 500 mL jar was charged with 122.5 g of IBU50 powder and 2.5 g of Aerosil R972 hydrophobic silica (2%). The jar was sealed and locked into the LabRAM platform clamp. The jar was vibrated at 60 Hz for 5 minutes at 70-75 G's.

Example 3

Ibuprofen IBU50 was dry coated with silica using a MAIC. A 120 mL jar was charged with 9.8 g of IBU50 and 0.2 g of Aerosil R972 hydrophobic silica (2%) and 5.0 g of 700-1400 μm barium ferrite magnetic granules (Aveka, Pa., USA). The jar was sealed and placed into an oscillating magnetic field powered by 20% of a 110V (60 Hz) power source. The magnetic granules were propelled by the oscillating magnetic field for 10 minutes. When finished, the magnetic granules were sieved out using a 355 μm sieve.

Example 4

Ibuprofen IBU90 was dry coated with silica using a FEM. 600 g of ibuprofen IBU90 was preblended with 2% of Aerosil R972 hydrophobic silica using the LabRAM. The preblended powder was then fed into the FEM with a calibrated screw feeder at 6 g/min. A venture-based feed nozzle operated at 10 psi sucked powder into the milling chamber while two grinding nozzles operated at 10 psi caused particle-particle collisions and particle wall collisions to mill the powders. The process was run in two 50-minute-batches to avoid overfilling the collection chamber. After each batch the powder was collected from the collection jar and exhaust filter separately. To produce a narrower size distribution the coated powders from the collection jar (coarser) and the exhaust chamber (finer, typically less than 20 microns) were not combined.

Example 5

The different dry coating methods were compared in a scale-up experiment, where 600 g of ibuprofen was dry coated with Aerosil R972 silica. The results are presented in Table 2. While all methods were capable of producing a well flowing ibuprofen powder, the LabRAM is especially convenient, because of the short processing times and ease of use/clean up. Using the LabRAM, 600 g of ibuprofen-silica particles was produced in only 1 hour, whereas almost 4 hours were required when processing in the small scale Comil. However, the Comil and FEM can be operated continuously, which may, in some embodiments, offer an advantage over batch methods such as LabRAM.

TABLE 2

Comparison of dry coating Equipment

| Equipment | Batch Size | Is it Scalable? | Processing time for 600 g | Outcome Comment |
|---|---|---|---|---|
| LabRAM | 10-125 g | Yes, batch | 1 hr | Produces mild heat (~50° C.) |
| MAIC | 10 g | No, batch | 10 hr | Magnetic Media Particles Present |
| Comil | 600 g | Yes, Continuous | 4 hr | Cohesive particles limit processing speed, High impeller speeds cause agglomeration |
| FEM | 250 g | Yes, Continuous | 6 hr | Used to produce coated micronized powders (<45 μm) |

Example 6

The flow properties of ibuprofen powders (IBU50 or IBU90) after dry coating were measured after coating with different types of silica and/or different coating processes (Table 3). The high angle of repose (AOR) value for the uncoated ibuprofen indicates that it has exceedingly poor flow, while the ibuprofen-silica particles all have significantly lower AOR values. Even the dry-coated ibuprofen powders with sizes nearly an order of magnitude lower than the uncoated (as received) powders have passable flow. M5P hydrophilic silica has a particle size of 20 nm and is manufactured by Cabot

TABLE 3

Flow properties of ibuprofen before and after dry coating

| Coating Material | Silica Concentration (%) | Method | D10, D50, D90 | | | AOR (°) |
|---|---|---|---|---|---|---|
| — | 0 | As Received | 26 | 76 | 186 | 55 |
| M5P | 2.0 | Comil | 25 | 74 | 173 | 39 |
| R972P | 2.0 | Comil | — | — | — | 39 |
| R972P | 2.0 | LabRAM | 25 | 74 | 170 | 39 |
| R972P, Ibu90 | 1.0 | FEM | 10 | 32 | 74 | 38 |

Example 7

Ibuprofen powder was dry coated with different silica particles (M5P, TS530 and R972P). When dry coated with hydrophobic silica, the ibuprofen-silica particles were poorly wetted and as a result the amount dissolved after 30 seconds in a low volume dissolution test was low. In comparison, when the ibuprofen powder was either not coated or coated with untreated hydrophilic silica, the ibuprofen-silica powder had a higher amount dissolved in 30 seconds in the same dissolution test. When coated with more hydrophobic TS530 (non-food grade) silica, significantly less dissolution was found in comparison to Aerosil R972P, which is less hydrophobic.

TABLE 4

Flow properties and dissolution of ibuprofen before and after dry coating

| Coating Material | Surface Chemistry | Silica Concentration (%) | Method | D10, D50, D90 | | | % Dissolved after 30 s |
|---|---|---|---|---|---|---|---|
| — | — | 0 | As Received | 26 | 76 | 186 | 77 |
| M5P | Hydrophilic | 2.0 | Comil | 25 | 74 | 173 | 92 |
| TS530 | Hydrophobic | 5.0 | MAIC | — | ~74 | — | 11 |
| R972P | Hydrophobic | 2.0 | Comil | — | ~74 | — | 73 |

Example 8

Diclofenac sodium powder with a core particle size of 23 µm was dry coated with 1% M5P hydrophilic silica, which has a particle size of 20 nm. The dry coating was carried out using a Comil, with various impeller speeds. The powder was sized before and after dry coating using a Rodos/Helos disperser and laser scattering based particle sizer (Sympatec Inc., NJ). The Rodos/Helos system uses a venturi nozzle to disperse the powders, where lower pressure typically deagglomerates powders while higher pressures potentially result in particle breakage. It can be seen in FIG. 3 that as the dispersion pressure increases from 0.1 to 1 bar, the uncoated powder particle size remained fairly constant. At higher dispersion pressures the powder particle size significantly decreased which indicated that the diclofenac sodium powder particles underwent attrition during the size measurement. After dry coating in the Comil, the diclofenac sodium powder was again sized. In this example, higher impeller speeds led to more agglomeration, possibly due to higher intensity shear at higher impeller speeds, which may fuse together the highly cohesive powders.

Example 9

Ibuprofen-silica particles were coated in a fluidized bed. 150 g of ibuprofen-silica particles, produced with a LabRAM, was charged into the fluidized bed bowl of a Mini-Glatt 9550 (Glatt, NJ, U.S.A, Germany). Air was first heated to 55° C. and then fed through the bottom of the conical fluidized bed, through a stainless steel sintered metal distributor plate with a 5 µm pore size (Mott Corporation, CT, USA). The fluidizing velocity was controlled to a superficial gas velocity of 5.33 cm/s (or about 30-40% of the gap between the d50 minimum fluidizing velocity and the d50 terminal velocity). To achieve these low fluidizing velocities, the heated air had to be diverted through the lower nozzle inlet indicated in FIG. 2 so that the low flow heater fail-safe was not triggered. Blowout air was pulsed through the 10 µm filter cartridges every 5 seconds to dislodge powder that may have stuck to the filter. A conical fluidized bed configuration was used to fluidize these fine ibuprofen-silica particles to ensure that the larger particles were fluidized without elutriating the fine particles.

The fluidized bed was heated to 28° C. at which point a polymer solution (suspension) was pushed with a peristaltic pump through a concentric nozzle with an inner nozzle (300 µm) at 1.26 mL/min. The spray was broken into droplets by unheated compressed air at 1.00 bar that passed through the outer nozzle (800 µm). The bed temperature was closely monitored and the inlet temperature was modified, if necessary, to ensure that the bed temperature was 26±1° C. Periodically the side of the column was hit with a rubber mallet to remove particles that stuck to the wall.

The fluidized bed was sprayed continuously until the ibuprofen-silica particles had been coated with a predetermined polymer solution volume. The spray was turned off and the bed was dried for several minutes until the bed temperature was above 28° C., at which point the fluidizing air and atomizing air were also stopped. The bed was opened and inspected for signs of excessive agglomeration, defluidization or caking on the filters. 3-5 g of sample was collected for sizing and imaging purposes. The fluidized bed coating process may be restarted if the polymer coating was insufficient. After the fluidized bed coating process was finished, the powder in the bowl was collected. Care was taken to not collect the powder that adhered to the filter or walls, as it was expected that these ibuprofen-silica particles would not be well coated.

Example 10

Ibuprofen-silica particles were coated in a fluidized bed with various polymers. The starting material was ibuprofen (d50=70 µm) that had been dry coated with 2% Aerosil R972 hydrophobic silica. The polymers are listed in Table 5, including a variety of water soluble, water insoluble and pH dependent polymers. The fluidized bed coating experiments described in Table 5 reflect the maximum amount of polymer loading achieved over a variety of experimental conditions. Taste masking was assessed by a three person taste panel, where the overall taste and presence of throat burn was categorized based on the group consensus. The taste classifications used were Poor, Moderate and Well.

TABLE 5

Fluidized bed coating with different polymer types

| Polymer type | Polymer Water Soluble | Polymer Water Insoluble | Solvent | Result Max Loading Attempted (%) | Result D50 (µm) | Result Taste Masking |
|---|---|---|---|---|---|---|
| pH Dependent <5 | — | E100 | 4.3 pH PBS or Ethanol | 2.4 | Defluidized | — |
| pH Dependent >7 | — | FS30D | DI water | 4.8 | Defluidized | — |
| Completely Insoluble | — | RS100 | Ethanol | 7.0 | Defluidized | Poor |
| Completely Insoluble | — | EC | Ethanol | 6.0 | >800 µm | Well |
| Partially Soluble | HPMC | EC | Water/ethanol | 11.7 | 130 µm | Moderate |
| Partially Soluble | HPMC | RS100 | Water/ethanol | 16.0 | 162 µm | Moderate |

The three Eudragit polymers (E100, FS30D, RS100) all resulted in the ibuprofen powder strongly adhering to the walls of the fluidized bed coating apparatus and eventual defluidization, leading to polymer loadings which were too low to impart sufficient taste masking to the ibuprofen powder.

Example 11

Coating of ibuprofen-silica composite particles was carried out in a fluidized bed. Several combinations of water insoluble and water soluble polymers were explored at various loadings to produce taste masking. These polymers were sprayed onto the ibuprofen-silica composite particles at the operating conditions described below in Table 6. The inlet air temperature, humidity and atomizing air pressure were all kept constant at 55° C., 10% relative humidity and 1.00 bar, respectively, for all experiments.

TABLE 6

Fluidized bed coating conditions for coating ibuprofen powders

| Experiment # | Polymer type | Solvent | Superficial fluidizing velocity (cm/s) | Sprayrate (mL/min) | Bed Temp (° C.) | Polymer Loading (%) | D10 (μm) | D50 (μm) | D90 (μm) |
|---|---|---|---|---|---|---|---|---|---|
| FBC-IBU-30 | 2.00% EC | EtOH | 3.3-10 | 0.69-0.84 | 28-31 | 3.6 | ~ | ~ | >800 |
| FBC-IBU-40 | 1.13% EC, 1.50% HPMC | 55% EtOH, 45% H$_2$O | 4.3 | 0.66 | 26-27 | 7.2 | 64 | 147 | 304 |
| FBC-IBU-58 | 1.13% RS100, 1.50% HPMC | 55% EtOH, 45% H$_2$O | 5.3 | 1.25 | 26-27 | 6.1 | 58 | 118 | 225 |
| FBC-IBU-59 | 100% RS100 | EtOH | 5.3 | 1.33 | 26-27 | 5.2 | 49 | 98 | 197 |
| FBC-IBU-57 | 1.13% RS100, 1.49% HPMC, 0.57% 180 nm SiO$_2$ | 55% EtOH, 45% H$_2$O | 5.3 | 1.25 | 26-27 | 16.1 | 81 | 163 | 289 |
|  | 2.00% RS100, | EtOH | 5.3 | 1.33 | 26-27 | 6 | 63 | 112 | 205 |

First, a single polymer layer coating system was produced by spraying ethyl cellulose onto ibuprofen-silica composite particles (FBC-IBU-30), which resulted in a well taste masked powder after only 3.6% polymer loading was applied. However the powder grew to a particle size that was greater than could be measured by the Rodos/Helos sizer (max size 800 μm) and resulted in a poor mouth feel. This large agglomerate size was likely due to the large spray droplet sizes that resulted from the high viscosity of the polymer solution.

Another single polymer layer coating system was produced by spraying a solution of insoluble Eudragit RS100 in ethanol onto the ibuprofen-silica composite particles (FBC-IBU-59). The agglomerate sizes were significantly reduced. However the bed defluidized before taste masking could be achieved.

Other single layer coating systems used a combination of a water insoluble polymer and a water soluble polymer blended into a water/ethanol mixture as solvent. These two systems achieved small ibuprofen agglomerate sizes without significant defluidization problems. Here, the ethylcellulose/HPMC (FBC-IBU-40) solution was sprayed at half of the spray rate of the Eudragit RS100/HPMC (FBC-IBU-58) solution and resulted in larger agglomerate sizes (as well as longer processing times) and still had larger particle sizes. However, the presence of the water soluble polymer made taste masking difficult to achieve at the attempted polymer loadings. Thus, an additional second polymer layer of water insoluble polymer will be required to achieve taste masking.

Figure 4:
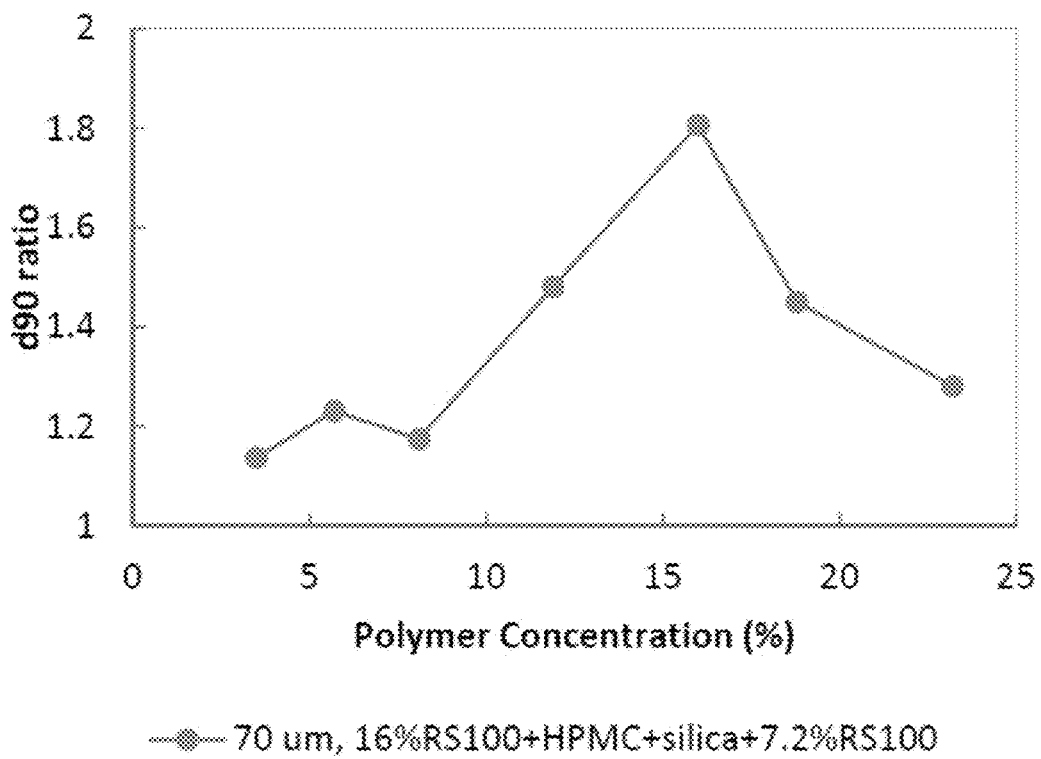
FIG. 4 is a plot of polymer loading versus agglomeration for a 70 µm core particle coated with 16% of Eudragit RS100, hydroxylpropyl methylcellulose (HPMC) and silica and 7.2% Eudragit RS100.

A two layer polymer coating system was produced by first using Eudragit RS100/HPMC/180 nm silica (FBC-IBU-57) to coat the ibuprofen-silica composite particles in a fluidized bed at a polymer loading of 16% to produce a first polymer layer on the ibuprofen-silica composite particles. A solution of Eudragit RS100 (insoluble in water) in ethanol was then sprayed to coat the first polymer layer on the ibuprofen-silica composite particles with a second polymer layer to achieve an additional weight gain of 6.1%. This second layer both significantly reduced the particle size to 112 μm and imparted significant taste masking, as shown in FIG. 4. The size reduction that occurred during the spraying of the Eudragit RS100 solution may have been caused by collisions between the agglomerates during fluidization as well as exposure to high shear in the spray nozzle.

Figure 5:
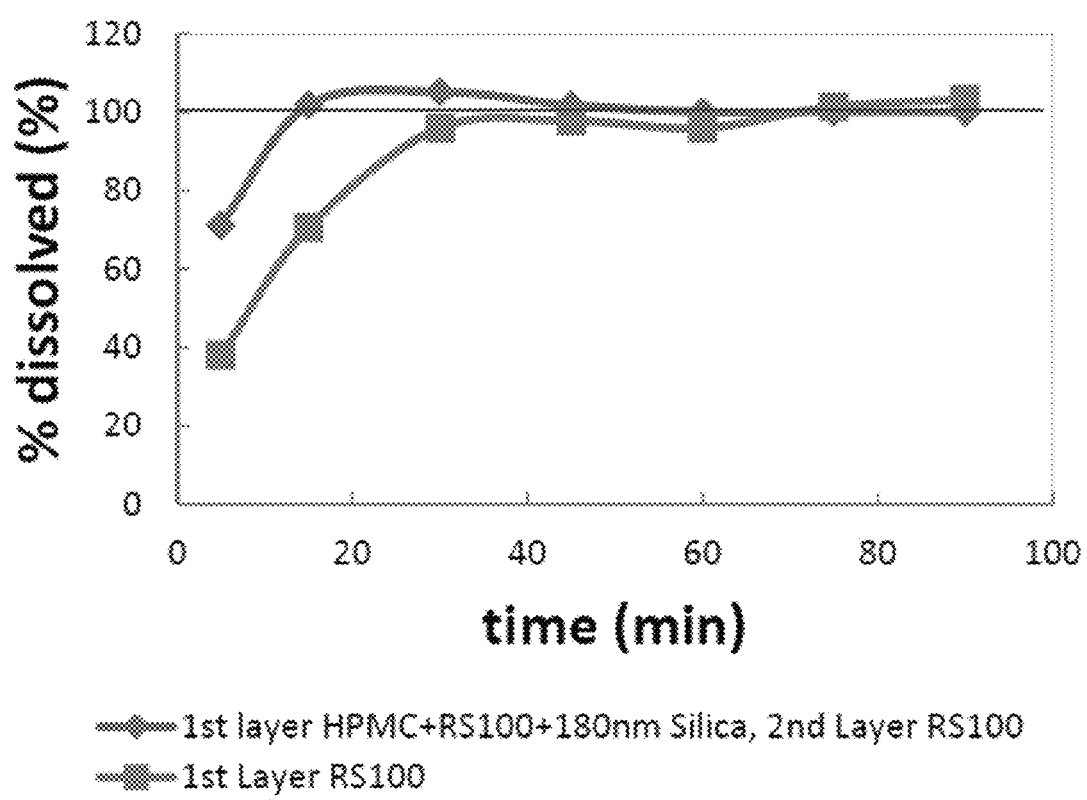
FIG. 5 depicts the dissolution profiles of taste masked ibuprofen powders.

FIG. 5 shows the dissolution profile of fluidized bed coated ibuprofen-silica composite particles from two separate experiments (FBC-IBU-57 for two polymer layers and FBC-IBU-59 for a single polymer layer system). USP Dissolution tests were performed. The particles with two polymer layers (FBC-IBU-57) produced a well taste masked powder with complete release of API in 15 minutes in the USP Dissolution Test. On the other hand, the ibuprofen-silica composite particles coated with a single, completely water insoluble polymer layer (FBC-IBU-59) required 45 minutes to achieve complete release in the USP Dissolution Test, and also provided poor taste masking.

Fluidized bed coating of ibuprofen-silica composite particles with a two layer polymer coating system: Eudragit RS100/HPMC as the inner layer and Eudragit RS100 as the outer layer, produced the highest quality taste masking with the smallest agglomerate size and an acceptable dissolution rate.

Example 12

The sprayed polymer solution was periodically blended with small amounts of silica as it was sprayed into the fluidized bed. 0.1 wt % silica (Aerosil R972p, Aerosil R974 or M5P) was gently stirred into the fluidized bed, paying special attention to break up the large chunks that formed during spraying of the second polymer solution. It was observed that the addition of silica helps reduce the cohesion between particles. When spraying of polymer solution onto fine powders leads to agglomeration, 0.1 wt % silica should be added to the bed after about every 2% by weight of polymer addition.

Example 13

Silica was added directly to the first polymer solution for a fluidized bed coating experiment. Ibuprofen-silica composite particles were coated in a fluidized bed with a polymer solution composed of 1.13% HPMC and 1.50% Eudragit RS100, and, optionally, 180 nm silica particles, in a solvent of ethanol and water, as described in Table 7. In all cases the ibuprofen-silica composite particle powder was processed using the following conditions: 150 g of ibuprofen-silica composite particles was fluidized at 2 cfm (5.3 cm/s) of dry air heated to 55° C. The polymer solution was sprayed at 1.26 mL/min and the resulting bed temperature was approximately 26° C. The agglomerate size of the silica particles was determined using dynamic light scattering (DelsaNano, Beckman Coulter, USA).

TABLE 7

Addition of silica in polymer solution

| Name | Silica | Polymer | Solvent | Silica Size (μm) |
|---|---|---|---|---|
| FBC-IBU-58 | No Silica | 1.13% RS100, 150% HPMC | 55% EtOH, 45% $H_2O$ | — |
| FBC-1BU-57 | Unstabilized Silica | 1.13% RS100, 1.49% HPMC | 55% EtOH, 45% $H_2O$ | — |
| FBC-IBU-65 | Stabilized Silica | 0.57% 180 nm $SiO_2$ | 55% EtOH, 45% 10 pH NaOH | 3.44 ± 0.76 |
| FBC-IBU-69 | | | 55% EtOH, 45% 2 pH $HNO_3$ | 1.29 ± 0.13 |
| FBC-IBU-66 | | 1.60% RS100, 2.10% HPMC, 0.81% 180 nm $SiO_2$ | 70% EtOH, 30% 10 pH NaOH | 1.22 ± 0.02 |

Figure 6:
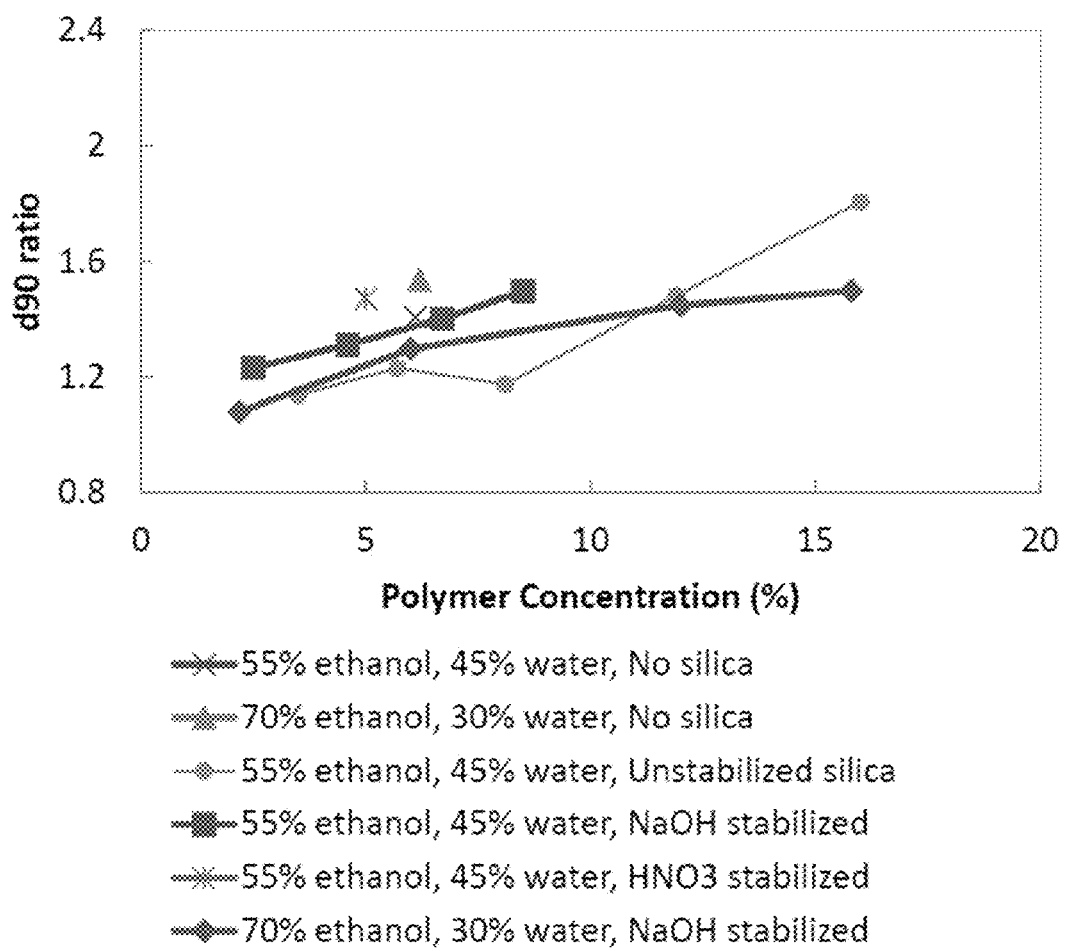
FIG. 6 depicts the effects of different silicas on ibuprofen agglomerate size.

The agglomerate size of the ibuprofen-silica particles is depicted as a function of polymer loading in FIG. 6. The inclusion of 180 nm (unstabilized) silica particles in the polymer solution significantly reduced the agglomerate sizes in comparison with experiments where no silica was used. However, the poor stability of the unstabilized silica in the water and ethanol solution resulted in periodic problems with nozzle clogging.

Figures 7A, 7B, 7C:
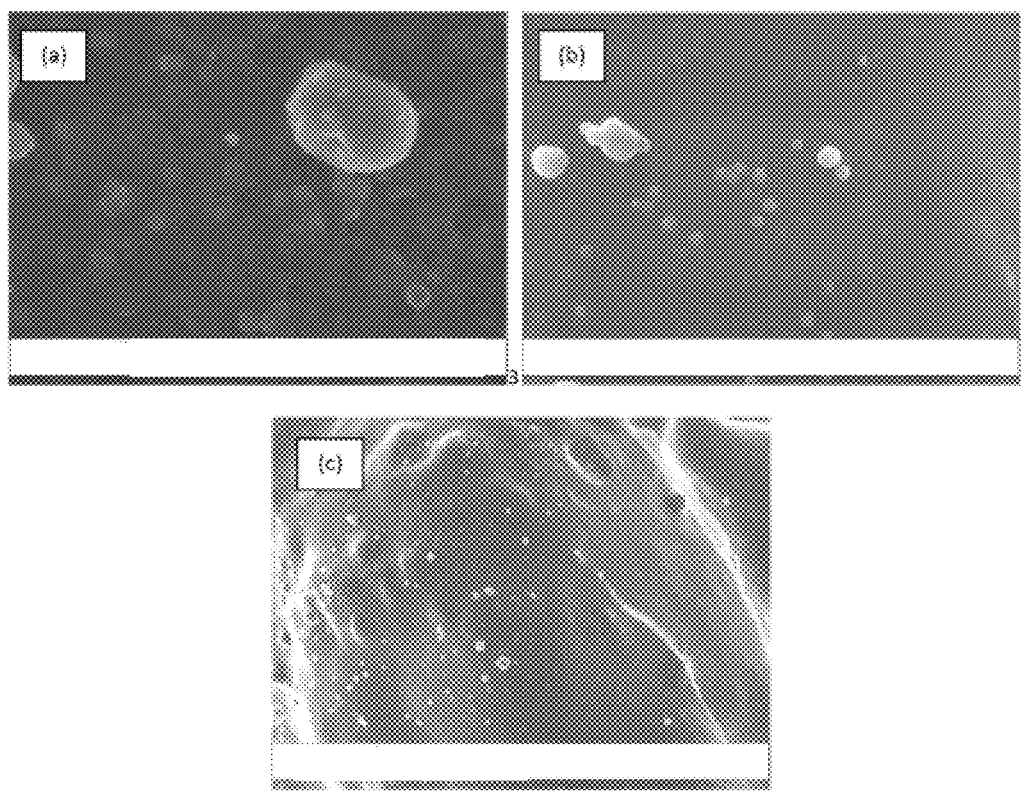
FIGS. 7a-7c show scanning electron microscope (SEM) images of fluidized bed coated ibuprofen particles.

Stabilized silica particles can effectively reduce nozzle clogging. Several different methods may be used to stabilize the silica particles. The stabilized silica was added to the first polymer solution, to provide a coated ibuprofen powder having less agglomeration (FIG. 6). SEM images of the ibuprofen coated with polymer solution containing the unstabilized silica and the stabilized (NaOH+70% ethanol) silica are shown in FIGS. 7a-7c. FIG. 7a (unstabilized silica) shows that the silica particles are well dispersed in the polymer coating. FIGS. 7b and 7c show that stabilized silica is dispersed throughout the entire polymer coating.

Figures 8A, 8B, 8C, 8D:
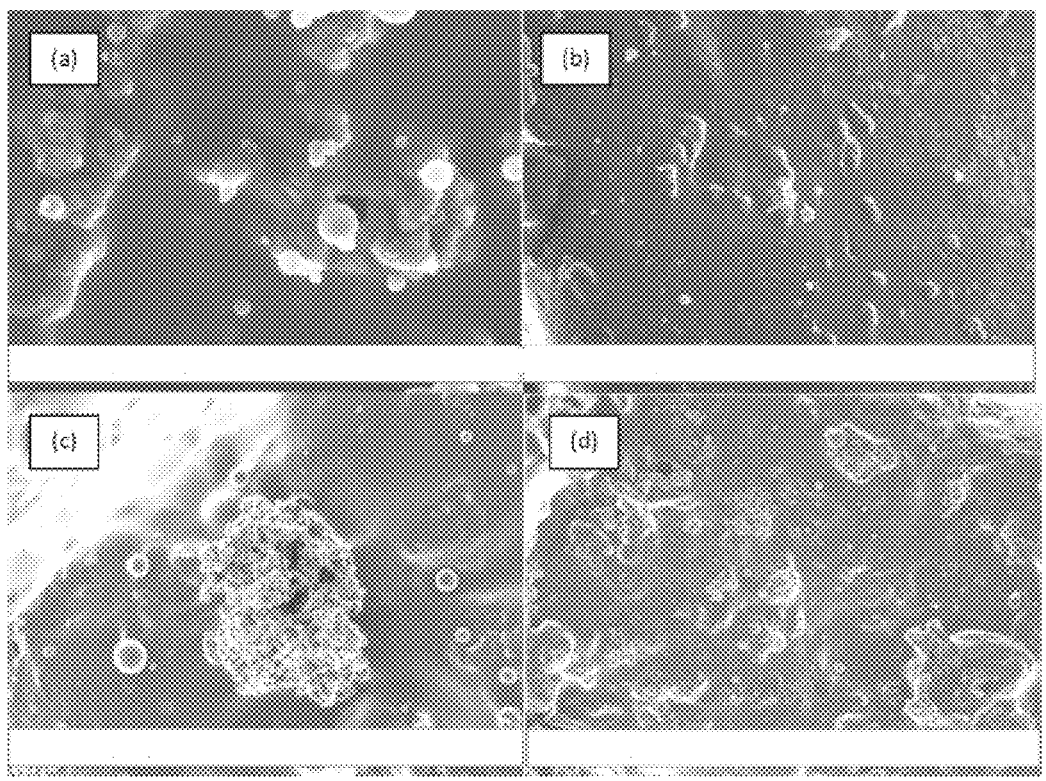
FIGS. 8a-8d show SEM images of fluidized bed coated ibuprofen particles.

Referring to FIGS. 8a and 8b, these figures show products made with silica stabilized with $HNO_3$, while FIGS. 8c and 8d show products made with silica stabilized with NaOH+55% ethanol. FIGS. 8a and 8c show ibuprofen-silica powder forming ~1 and ~4 μm silica agglomerates, respectively. FIGS. 8b and 8d show that these silica agglomerates were poorly dispersed throughout the polymer layer.

Example 14

Figure 9:
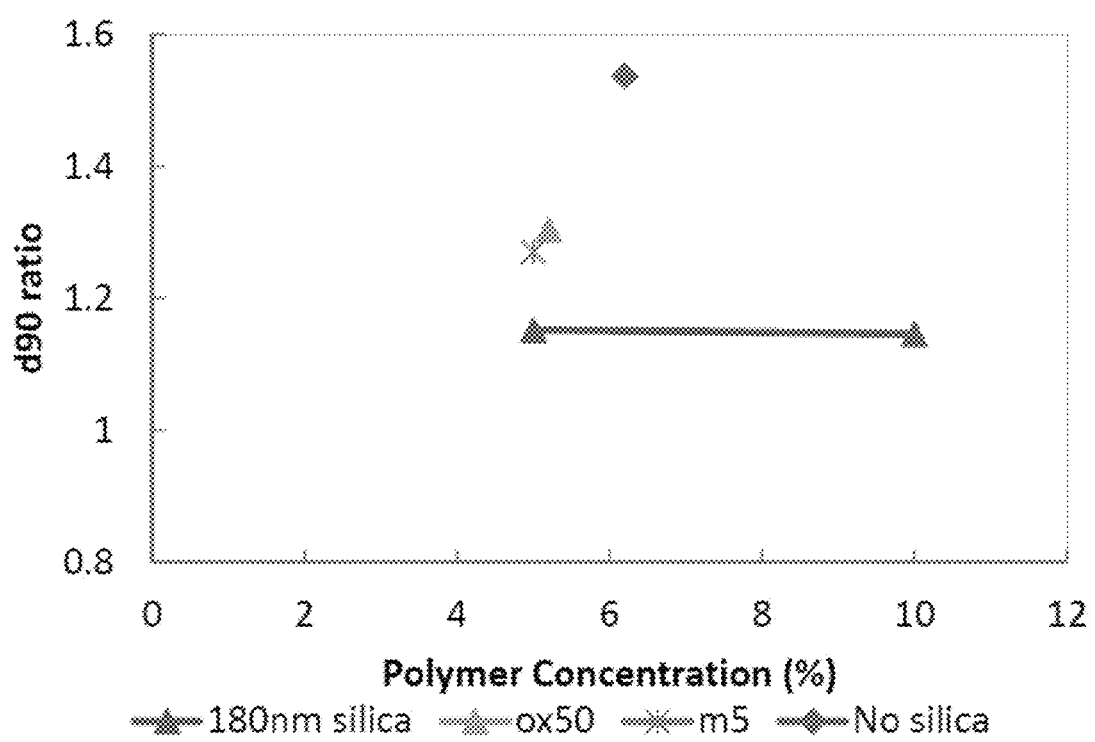
FIG. 9 is a plot of polymer concentration versus ibuprofen particle agglomerate size using different types of silicas as coating materials.
Figures 10A, 10B, 10C:
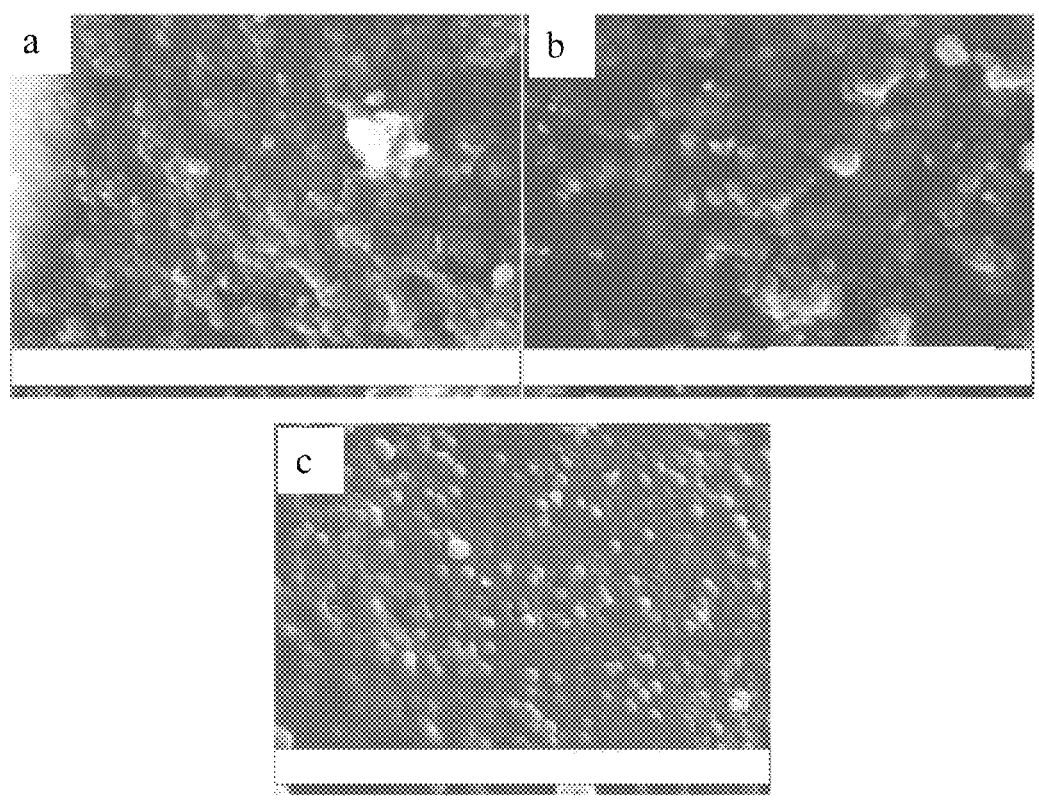
FIGS. 10a-10c show SEM images of fluidized bed coated ibuprofen particles.

Three silica types were used in the first polymer solution to minimize ibuprofen agglomeration during the fluidized bed coating step. Two are Cab-o-sil m5 and Aerosil Ox50, which have the added benefit of being produced by vapor phase hydrolysis and are therefore considered GRAS (generally regarded as safe) by the FDA. The other is 180 nm silica. The experimental procedure was the same as for Example 13. As shown in FIG. 9, the use of either of the silicas produced by vapor phase hydrolysis significantly reduced the agglomeration in comparison to when no silica was used. The use of 180 nm silica was able to keep the agglomerate size lower than when the smaller silica nano-particles were used. FIGS. 10a-10c show the SEM images of the surface of the polymer/silica coated ibuprofen. When the smaller silica particles were used (FIGS. 10a with Cab-o-sil; and 10b with OX50), thick layers of silica particles were bound together with polymer. On the other hand, when 180 nm silica particles were used (FIG. 10c), they tended to be discrete and dispersed on ibuprofen-silica particles.

Example 15

Fluidized bed coating of ibuprofen-silica particles was carried out under various experimental conditions (Table 8). The spray rates and superficial fluidizing velocities were varied to explore their effects on the growth of ibuprofen particle agglomerates. In all cases the inlet air temperature was chosen to keep the bed temperature close to 26° C. At lower bed temperatures, the ibuprofen particle may significantly agglomerate and defluidize at low polymer loadings.

Figure 11:
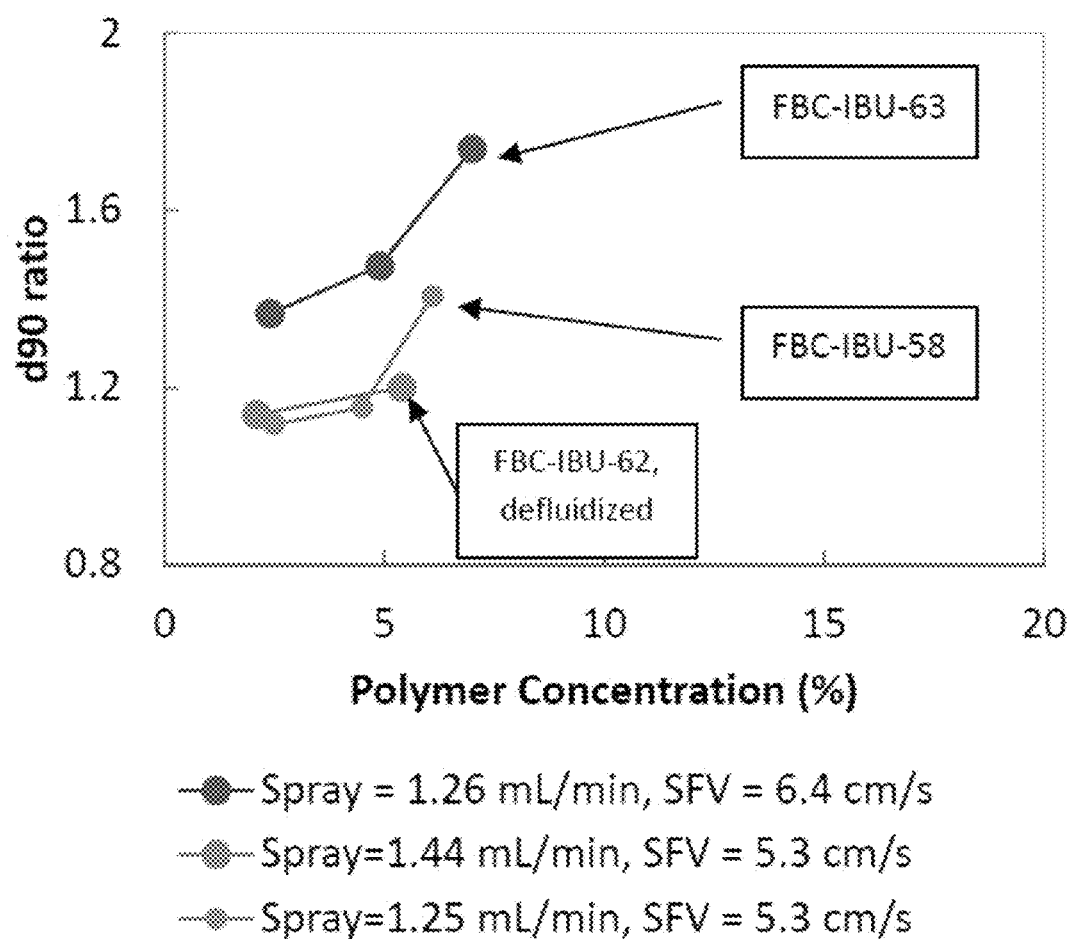
FIG. 11 is a plot of polymer concentration versus ibuprofen particle agglomerate size showing the effect of different spraying conditions for coating the particles.
Figure 12:
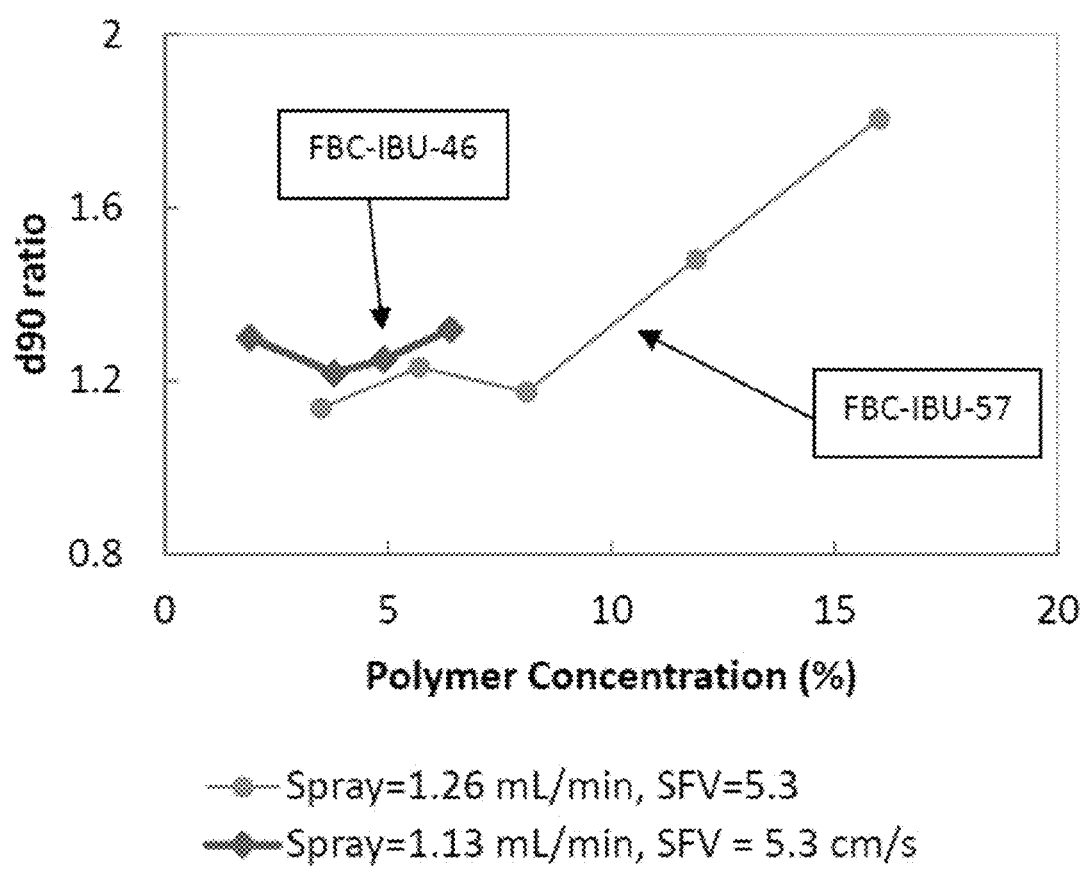
FIG. 12 is another plot of polymer concentration versus ibuprofen particle agglomerate size showing the effect of different spraying conditions.
Figure 13:
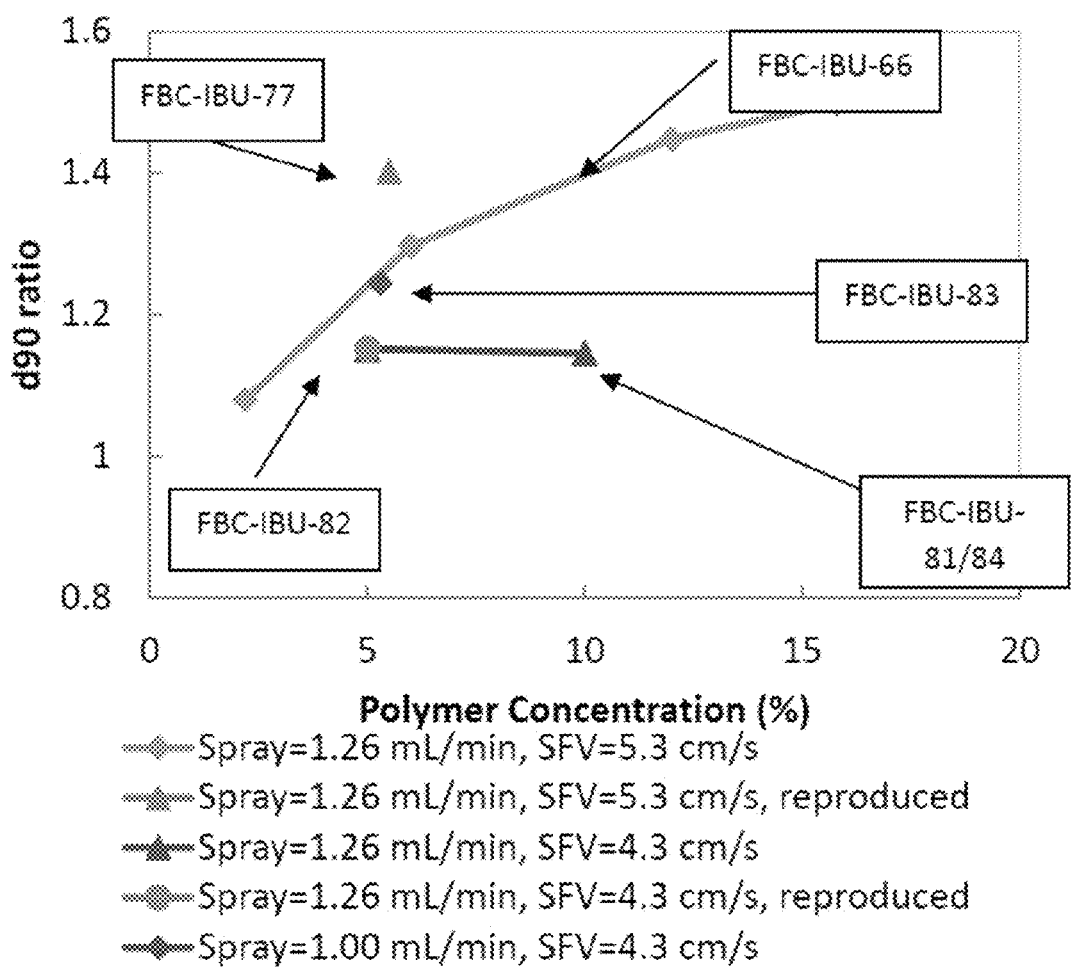
FIG. 13 is a plot of polymer concentration versus ibuprofen particle agglomerate size for different spaying conditions.

The effect of these experimental conditions are shown in FIGS. 11-13, which depict ibuprofen particle agglomeration when the polymer solution contained no silica, unstabilized silica and silica stabilized with NaOH, 70% ethanol, respectively. It was observed that the d90 ratios of the ibuprofen coated with the first polymer solution without silica (FIG. 11) were larger than when silica was included (FIGS. 12 and 13).

TABLE 8

Fluidized bed coating conditions and the agglomerate size of ibuprofen

| Name | Suspension Sprayed | Polymer | Superficial fluidizing velocity (cm/s) | Fluidizing Flowrate (cfm) | Sprayrate (mL/min) | Bed Temperature (° C.) | Inlet Air Temperature (° C.) |
|---|---|---|---|---|---|---|---|
| FBC-IBU-58 | No Silica | 1.13% RS100, 1.50 HPMC | 5.3 | 2 | 1.26 | 26-28 | 55 |
| FBC-IBU-62 | | | 5.3 | 2 | 1.44 | 22-24 | 65 |
| FBC-IBU-63 | | | 6.4 | 2.4 | 1.26 | 26-28 | 55 |
| FBC-IBU-46 | Unstabilized Silica | 1.13% RS100, 1.49% HPMC, 0.57% 180 nm $SiO_2$ | 5.3 | 2 | 0.95-1.13 | 26-28 | 55 |
| FBC-IBU-57 | | | 5.3 | 2 | 1.25 | 26-27 | 55 |
| FBC-IBU-66 | Stabilized Silica (NaOH, 70% ethanol) | 1.50% RS100, 2.10% HPMC, 0.81% 180 nm | 5.3 | 2 | 1.26 | 25-27 | 55 |
| FBC-IBU-77 | | | 5.3 | 2 | 1.26 | 25-27 | 55 |
| FBC-IBU-81/84 | | | 4.3 | 1.6 | 1.26 | 25-27 | 65 |

TABLE 8-continued

Fluidized bed coating conditions and the agglomerate size of ibuprofen

| Name | Suspension Sprayed | Polymer | Superficial fluidizing velocity (cm/s) | Fluidizing Flowrate (cfm) | Sprayrate (mL/min) | Bed Temperature (° C.) | Inlet Air Temperature (° C.) |
|---|---|---|---|---|---|---|---|
| FBC-IBU-82 | | SiO$_2$ | 4.3 | 1.6 | 1.26 | 25-27 | 65 |
| FBC-IBU-83 | | | 4.3 | 1.6 | 1.00 | 25-27 | 60 |

The agglomerate size of ibuprofen particles grew faster, with respect to polymer loading, at lower spray rates, as shown in FIG. 12 (FBC-IBU-46 was larger than FBC-IBU-57 at the same polymer loadings) and FIG. 13 (FBC-IBU-83 was larger than FBC-IBU-81/84 and FBC-IBU-82). An increase in the spray rate from 1.26 mL/min (FBC-IBU-57) to 1.44 mL/min (FBC-IBU-62), as shown in FIG. 11, resulted in comparable agglomerate sizes. However at the higher spray rate, the bed defluidized at low polymer loadings. A balance should be maintained between the excessively dry conditions (at low spray rates) that may result in electrostatic charging and the excessively wet conditions (at high spray rates) where the polymer could be sprayed faster than it could be dried by the fluidizing air.

The ibuprofen agglomerates also grew faster at higher superficial fluidizing velocities, as shown in FIG. 11 (FBC-IBU-63 was larger than FBC-IBU-58) and FIG. 13 (FBC-IBU-66 and FBC-IBU-77 were larger than FBC-IBU-81/84 and FBC-IBU-82). This may be due to two main factors. The first factor was the excessively dry conditions that occur at higher fluidizing velocities (i.e. higher flow rates), which may cause charging to particles, leading to agglomeration. The second factor was that fine ibuprofen particles may be elutriated from the system or caked onto the filters at higher fluidizing velocities, which may increase agglomerate size of the ibuprofen powder in the bed by eliminating the fine ibuprofen particles and resulted in higher than recorded polymer loadings. The loss of the fine ibuprofen particles to the filters and the exhaust may not be reproducible as shown by FIG. 13. Reproduced experiments performed at higher fluidization velocities resulted in very different ibuprofen powder particle sizes (FBCIBU-66 and FBC-IBU-77), whereas similar repeated experiments at low velocities resulted in very similar agglomerate particle sizes (FBC-IBU-81/84 and FBC-IBU-82).

Example 16

Further experiments were conducted to illustrate the influence of the fluidizing velocity on the ibuprofen-silica particle size distribution. Here two types of excess fluidizing velocities were explored: (1) the excess fluidizing velocity, which referred to the difference between the actual fluidizing velocity (in the cylindrical section) and the minimum fluidizing velocity of the median particle size; (2) the excess conveying velocity which is the difference between the actual fluidizing velocity and the terminal velocity of the d10 particle size. The particle span is a dimensionless ratio that refers to the width of the particle size distribution ((d90−d10)/d50) and is comparable to the standard deviation of the size distribution. Typically, particle size distributions with large particle spans have very broad distributions that include both fine particles and coarse particles. The experimental conditions are listed in Table 9. In all cases, about 5% of polymer was sprayed onto the ibuprofen-silica particles.

Figure 14:
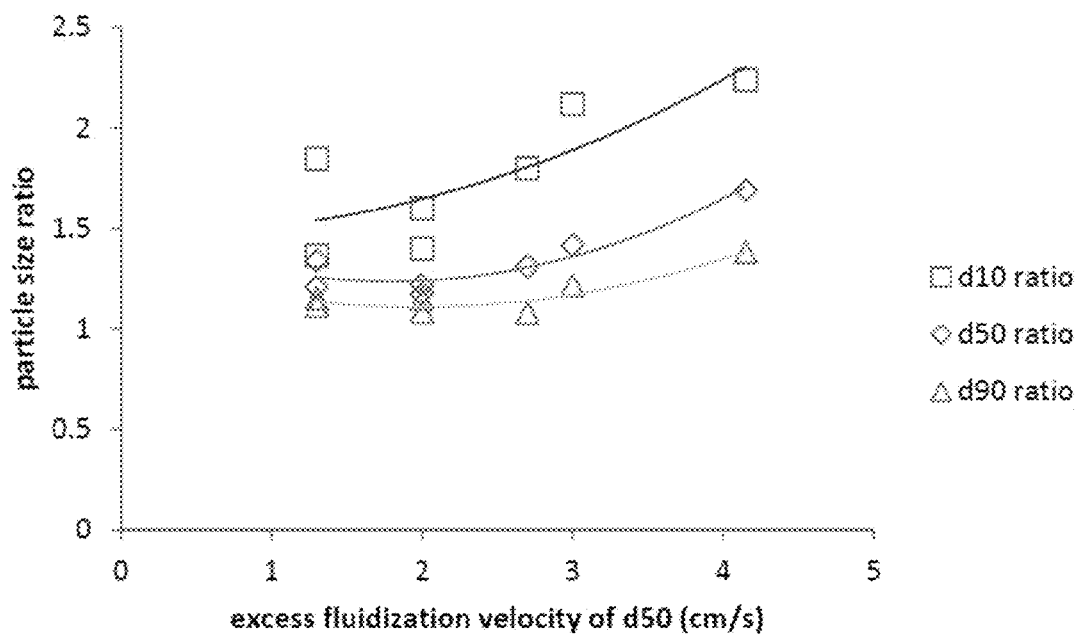
FIG. 14 is a plot of excess fluidization velocity versus ibuprofen particle agglomerate size.
Figure 15:
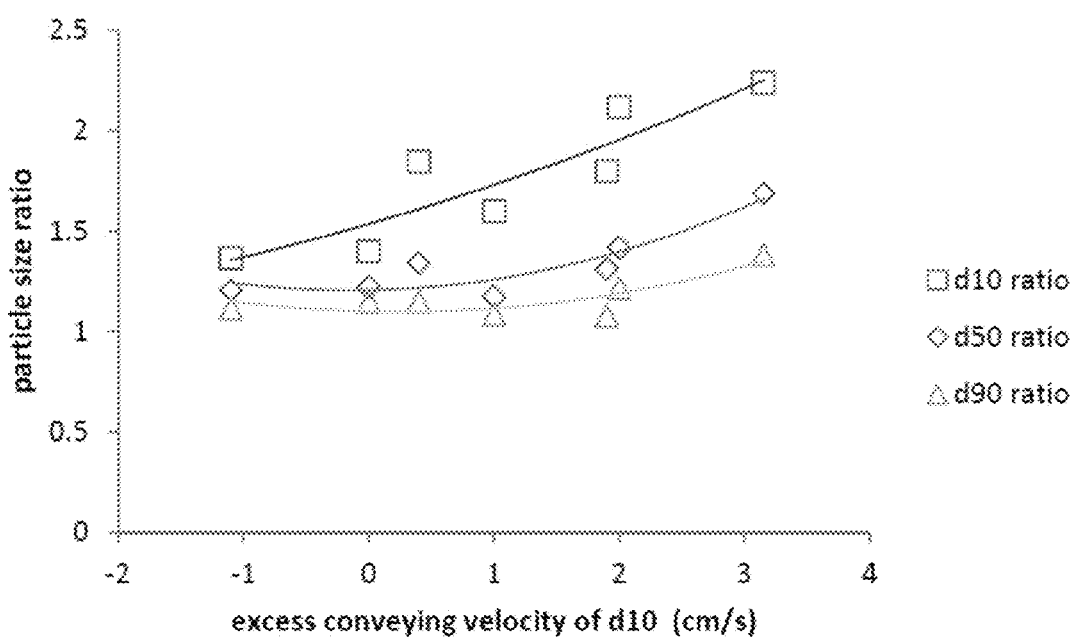
FIG. 15 is a plot of excess conveying velocity versus ibuprofen particle agglomerate size.
Figure 16:
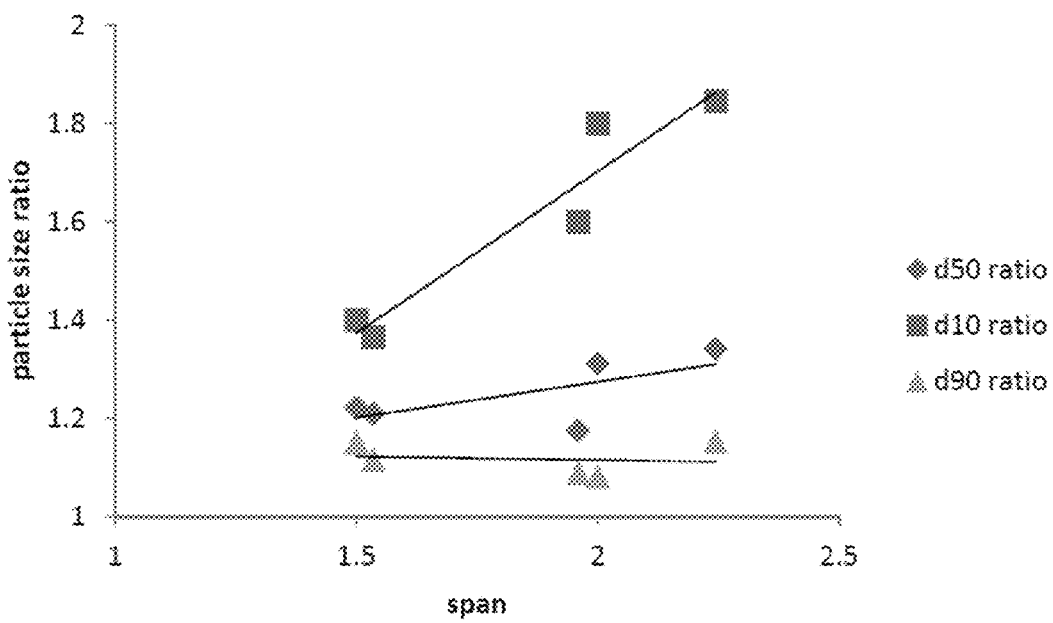
FIG. 16 is a plot of initial ibuprofen particle distribution span versus ibuprofen particle agglomerate size.

The experimental results are shown in FIGS. 14-16. Trend lines shown in these figures are for clarity purposes only. As shown in FIGS. 14-15, the d10, d50 and the d90 size ratios all generally increased with excess fluidizing velocity and excess conveying velocity. The size growth may be at least partially due to the elutriation of fine particles at high fluidization velocities and electrostatic charging in the excessively dry conditions at high fluidization velocities. The particle size ratios were nearly constant until the excess fluidization or excess conveying velocity exceeded 2.5 cm/s or 1 cm/s respectively. Thus, maintaining the excess velocities within these limits may minimize agglomeration in the fluidized bed by limiting elutriation and charging induced agglomeration.

It was observed that the d10 ratio grew more rapidly than the d50 ratio or the d90 ratio. This was likely due to the fact that the small particles were more likely to either leave the system through elutriation or attach onto one of the larger particles. While this may have a significant effect on the fine particles, it has little effect on the larger particles, because these fine particles offer only a minor contribution to the overall particle sizes in comparison to the larger particles.

As shown in FIG. 16, as the span of the initial ibuprofen-silica particle size distribution increased, the overall agglomerate size also increased, as evidenced by increasing d10 and d50 size ratios. These results indicate that wide size distributions for ibuprofen powder particles that include both fine and coarse particles were more likely to agglomerate than narrower size distributions. This may be due to attaching of the fine particles to the large particles. Considering that the largest particles volume only changed minutely, it would not have a significant effect on the d90 ratio. On the other hand, the removal of the finest particles can significantly alter the d10 ratio.

TABLE 9

Size distribution of ibuprofen particles when about 5% polymer was sprayed

| Sample | D50 (μm)/ Span | Excess fluid vel, d50 (cm/s) | Excess conveying vel, d10 (cm/s) | Size ratios | | |
|---|---|---|---|---|---|---|
| | | | | D10 ratio | D50 ratio | D90 ratio |
| FBC-IBU-81 | 74/2 | 2.0 | 1.0 | 1.60 | 1.17 | 1.09 |
| FBC-IBU-63 | | 4.2 | 3.2 | 2.24 | 1.69 | 1.38 |

TABLE 9-continued

Size distribution of ibuprofen particles when about 5% polymer was sprayed

| Sample | D50 (μm)/ Span | Excess fluid vel, d50 (cm/s) | Excess conveying vel, d10 (cm/s) | Size ratios | | |
|---|---|---|---|---|---|---|
| | | | | D10 ratio | D50 ratio | D90 ratio |
| FBC-IBU-66 | | 3.0 | 2.0 | 2.12 | 1.42 | 1.22 |
| FBC-IBU-85 | 41/2.2 | 1.3 | 0.4 | 1.85 | 1.34 | 1.15 |
| FBC-IBU-51/52 | 32/2.0 | 2.7 | 1.9 | 1.80 | 1.31 | 1.08 |
| FBC-IBU-86 | 86/1.5 | 1.3 | −1.1 | 1.37 | 1.21 | 1.12 |
| FBC-IBU-90 | 54/1.5 | 2.0 | 0.0 | 1.40 | 1.22 | 1.15 |

Example 17

Experiments were conducted to illustrate the effects of spray conditions on fluidized bed coating of ibuprofen-silica composite particles (Table 10). Here the fluidization velocities were scaled to maintain the excess fluidization velocities around 2 cm/s and the excess conveying velocity below 1 cm/s for ibuprofen-silica particles of various sizes. The spray rates were also scaled relative to total fluidizing velocities to avoid excessively wet or dry conditions. The experiments varied the spray droplet size by changing the atomization pressure.

Example 18

Figure 17:
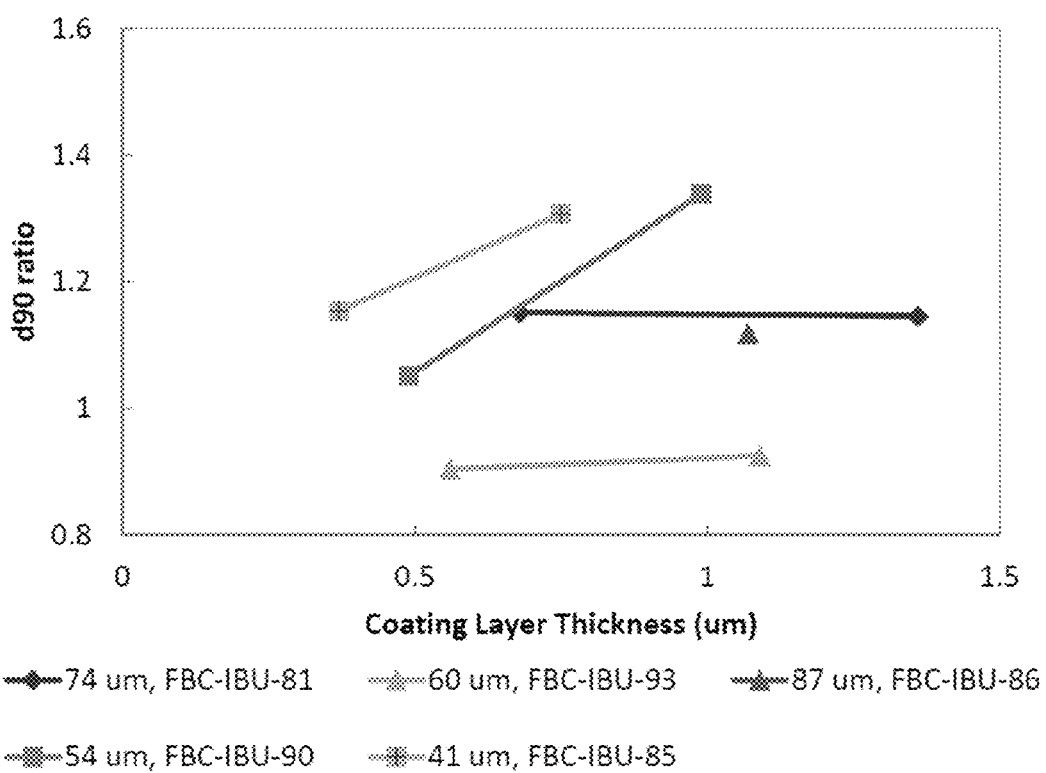
FIG. 17 is a plot of polymer coating thickness versus ibuprofen particle size to show the effective of coating different sized particles.

Fluidized bed coating of ibuprofen-silica composite particles was conducted to illustrate the relationship between ibuprofen particle agglomeration and polymer layer thickness. The results of the experiments are shown in FIG. 17 where the d90 ratio was described as a function of the coating layer thickness. During these experiments, the ratio of the total fluidization velocity to the spray rate was kept constant at about 3.4 to prevent overly dry or wet conditions. There was a general trend of faster growth as the ratio between the

TABLE 10

Spraying conditions and different ibuprofen particle sizes

| Sample | D50 (μm)/ Span | Characteristic Fluidizing velocities (cm/s) | | | Spray Properties | | | |
|---|---|---|---|---|---|---|---|---|
| | | Excess fluid vel, d50 | Excess convey vel, d10 | Total Fluidizing velocity | Sprayrate (mL/min) | Atomization pressure (bar) | Droplet Size (μm) | Ratio of droplet to initial size |
| FBC-IBU-81 | 74/2 | 2.0 | 1.0 | 4.3 | 1.26 | 1.00 | 9.4 | 0.13 |
| FBC-IBU-86 | 86/1.5 | 1.3 | −1.1 | 4.3 | 1.26 | 1.00 | 9.4 | 0.11 |
| FBC-IBU-90 | 54/1.5 | 2.0 | 0.0 | 3.3 | 0.95 | 0.95 | 9.4 | 0.17 |
| FBC-IBU-92 | 60/1.5 | 1.7 | −1 | 3.3 | 0.97 | 1.36 | 7.8 | 0.13 |
| FBC-IBU-85 | 41/2.2 | 1.3 | 0.4 | 2.1 | 0.61 | 1.00 | 8.4 | 0.20 |

The same polymer solution was used during these experiments (same as FBC-IBU-81). The droplet size was determined by directing the spray into the open optical chamber of a Spraytec (Malvern, MA, USA) laser scattering size measurement device. The relationship between the droplet size, spray rate and atomization pressure is described by Equations 3 and 4 below, where the d50 and d90 size are in μm, S is the spray rate in mL/min and P is the pressure in psig. This relationship is accurate for spray rates between 0.5-2.3 mL/min and atomization pressures of 10-20 psig. In some experiments, deviations as large as 10% may be observed between experimental values and predicted results.

The small final ibuprofen particle sizes observed in FBC-IBU-92 sample (Table 10) may be caused by deagglomeration induced by the high atomization pressure in the spray nozzle (1.36 bar as opposed to ~1.00 bar) which could introduce intense shear capable of breaking up loosely formed agglomerates.

$d50$ of droplet size with respect to spray rate and atomization pressure: $d50 = 28.16 + 1.056S - 2.228P + 0.05787P^2$     Equation 3

$d90$ of droplet size with respect to spray rate and atomization pressure: $d90 = 78.04 + 1.84S - 6.361P + 0.1629P^2$     Equation 4 droplet size and the initial ibuprofen median size increases. This effect was not caused by the initial ibuprofen particle size (i.e. larger ibuprofen particles will have thicker layers when the same amount of polymer is coated onto the surface, because of the smaller surface area per unit of ibuprofen).

Example 19

Figure 18:
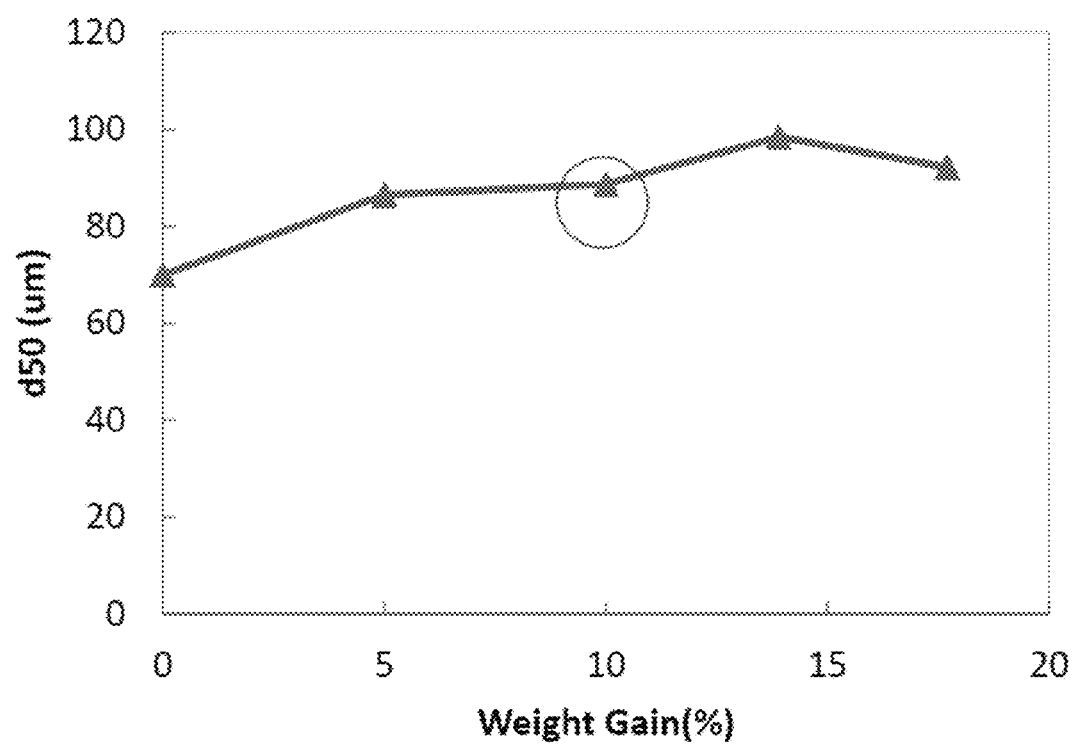
FIG. 18 is a plot of ibuprofen particle agglomerate size as a function of weight gain.

It has been observed that FBC-IBU-81/84 was an excellent fluidized bed coating formulation (see Table 8). This formulation was used to coat, using a fluidized bed, ibuprofen-silica composite particles that have been dry coated by LabRAM. The formulation comprises a partially water soluble first polymer layer and a water insoluble second polymer layer. 150 g of ibuprofen, previously dry coated with 2% Aerosil R972 in the LabRAM, was charged into the fluidized bed coating chamber and sprayed using the conditions described in Table 11. While spraying the second polymer solution, 0.1% Aerosil R972 silica was periodically blended into the fluidized bed to minimize adhesion of the coated powder to the wall. The addition of the silica would also prevent storage problems later. It can be seen from FIG. 18 that the final particle size was only 92 μm.

TABLE 11

Fluidized bed coating with two polymer layers

| Name | Suspension Sprayed | Polymer | Final Weight Gain (%) | Superficial fluidizing velocity (cm/s) | Fluidizing Flowrate (cfm) | Sprayrate (mL/min) | Bed Temperature (° C.) | Inlet Air Temperature (° C.) |
|---|---|---|---|---|---|---|---|---|
| 1st layer | Stabilized Silica (30% NaOH, 70% ethanol) | 1.60% RS100, 2.10% HPMC, 0.81% 180 nm SiO$_2$ | 10 | 4.3 | 1.6 | 1.26 | 25-27 | 65 |
| 2nd layer | (30% water, 70% ethanol) | 1.60% RS100 | 7.7 | 4.3 | 1.6 | 1.33 | 25-27 | 68 |

Example 20

To prevent adhesion and caking during storage of taste masked ibuprofen particles, experiments were carried out wherein silica particles were mixed with the fluidized bed coated ibuprofen-silica-polymer powders (with two polymer layers). 1% Aerosil R972 silica was dry coated onto the taste masked ibuprofen powder in the LabRAM at 50 G's for 30 seconds, which produced a well flowing taste masked ibuprofen powder.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A process for preparing a taste masked particulate pharmaceutical formulation from core particles that comprise an active pharmaceutical ingredient and at least a partial coating of nanoparticle material that has a median particle size not greater than 100 nm, comprising steps of:
   1) coating the core particles in a fluidized bed with a first polymer layer; and
   2) coating the first polymer layer of the core particles with a water insoluble second polymer layer in a fluidized bed in the presence of a nanoparticle material with a median particle size not greater than 100 nm; and
wherein the first polymer layer is at least partially water soluble.

2. The process of claim 1, wherein the step of coating the core particles with the first polymer layer comprises spraying a polymer solution in an amount sufficient to achieve a polymer loading of from 2 wt. % to 15 wt. % of the particulate pharmaceutical formulation.

3. The process of claim 2, wherein the step of coating the first polymer layer with a second polymer layer comprises spraying a second polymer solution in an amount sufficient to achieve to achieve a polymer loading of from 2 wt. % to 20 wt. % of the particulate pharmaceutical formulation.

4. The process of claim 1, wherein the first polymer layer comprises a water soluble polymer.

5. The process of claim 1, wherein the first polymer layer comprises a polymer selected from the group consisting of hydroxypropyl methylcellulose, hydroxypropyl cellulose, polyvinylpyrrolidone, polyvinyl alcohol, ammonio methacrylate copolymer, ethylcellulose and combinations thereof.

6. The process of claim 1, wherein the step of coating the core particles with the first polymer layer is carried out in the presence of nanoparticle material having a median particle size in the range of 100 nm to 500 nm.

7. The process of claim 6, wherein a median droplet size of the sprayed polymer solutions is independently selected from a median droplet size in the range of 5 μm to 15 μm.

8. The process of claim 6, further comprising the step of coating the second polymer layer with at least a partial coating of nanoparticle material.

9. The process of claim 1, wherein the second polymer layer comprises a water insoluble polymer selected from the group consisting of ammonio methacrylate copolymer, ethylcellulose, cellulose acetate and, and combinations thereof.

10. The process of claim 1, wherein a spray rate of the first and second polymer solutions is independently selected from a spray rate in the range from 0.5 ml/minute to 5 ml/minute.

11. The process of claim 10, wherein a fluidizing flow rate of the first polymer solution and the second polymer solution is independently selected from a fluidizing flow rate in the range of from 0.1 cfm to 5 cfm.

12. The process of claim 10, wherein the first polymer solution and the second polymer solution are each atomized at an atomization pressure independently selected from within a range of 5 psig to 35 psig.

13. The process of claim 1, wherein a fluidizing velocity in the range of from 1 cm/s to 10 cm/s is maintained during the steps of coating with the first and second polymer solutions.

* * * * *